United States Patent
Liu et al.

(10) Patent No.: US 11,624,738 B1
(45) Date of Patent: Apr. 11, 2023

(54) THREE-DIMENSION UNCONVENTIONAL RESERVOIR MONITORING USING HIGH-RESOLUTION GEOCHEMICAL FINGERPRINTING

(71) Applicant: REVOCHEM LLC, Houston, TX (US)

(72) Inventors: Yifei Liu, Houston, TX (US); Jiang Wu, Houston, TX (US)

(*) Notice: Subject to any disclaimer, the term of this patent is extended or adjusted under 35 U.S.C. 154(b) by 0 days.

(21) Appl. No.: 16/813,914

(22) Filed: Mar. 10, 2020

Related U.S. Application Data

(63) Continuation of application No. 16/392,109, filed on Apr. 23, 2019, now Pat. No. 10,585,078.

(60) Provisional application No. 62/837,119, filed on Apr. 22, 2019, provisional application No. 62/837,114, filed on Apr. 22, 2019, provisional application No. 62/671,510, filed on May 15, 2018, provisional application No. 62/661,109, filed on Apr. 23, 2018.

(51) Int. Cl.
*G01N 30/86* (2006.01)
*G01N 30/02* (2006.01)
*G01N 33/28* (2006.01)

(52) U.S. Cl.
CPC ..... *G01N 30/8686* (2013.01); *G01N 33/2823* (2013.01); *G01N 2030/025* (2013.01)

(58) Field of Classification Search
CPC ........... G01N 30/8686; G01N 33/2823; G01N 2030/025; E21B 49/00; E21B 41/0092; E21B 43/16; E21B 43/14; G01V 99/005; G01V 1/30; G01V 11/00; G01V 2210/1234; G06N 3/02; G06N 20/00; G05B 13/028

USPC ....... 166/250.01, 250.06; 436/25, 29; 702/6, 702/11, 13–14, 22, 188
See application file for complete search history.

(56) References Cited

U.S. PATENT DOCUMENTS 4,996,421 A * 2/1991 Rai ............... G01N 21/3563
250/253
6,634,211 B1* 10/2003 Blumberg .......... G01N 30/8658
210/659

(Continued)

*Primary Examiner* — Jeffrey P Aiello
(74) *Attorney, Agent, or Firm* — Wayne Edward Ramage; Baker Donelson

(57) ABSTRACT

Methods and systems to monitor and analysis unconventional reservoirs with wellbores with a substantially horizontal section. Monitoring and analysis is conducted in three dimensions using high-resolution geochemical fingerprinting analyses of rock samples and produced oil samples. The invention uses methods to preserve, prepare, extract, and/or analyze hydrocarbons in the pore spaces of or adsorbed in organic-rich rock samples, such as, but not limited to, drill cuttings and drill cores, using one or more combinations of physical energy sources, including, but not limited to, thermal, vapor pressure, and mechanical stress. The collected samples are transported and prepared in low temperature conditions, with parts of subsequent processing at very low temperatures, thereby allowing a fuller measurement of geochemical fingerprints for the extracted hydrocarbons using various analysis tools. More particularly, the treatment and process allows geochemical fingerprinting to very low carbon number ranges. The techniques of the present invention may be used to optimize well stacking and spacing, completion design, and cluster efficiency evaluation to improve unconventional reservoir economics.

4 Claims, 20 Drawing Sheets

(56) References Cited

U.S. PATENT DOCUMENTS

| | | | |
|---|---|---|---|
| 2005/0223658 A1* | 10/2005 | Reed | B29C 70/305 |
| | | | 52/102 |
| 2009/0081805 A1* | 3/2009 | Chau | G01N 30/8675 |
| | | | 436/161 |
| 2012/0232859 A1* | 9/2012 | Pomerantz | G01V 1/282 |
| | | | 703/2 |
| 2013/0060477 A1* | 3/2013 | Sen Gupta | G16C 20/20 |
| | | | 702/19 |
| 2013/0080133 A1* | 3/2013 | Sung | G01V 99/005 |
| | | | 703/10 |
| 2013/0282288 A1* | 10/2013 | Quinn | G01V 3/38 |
| | | | 702/7 |
| 2015/0204176 A1* | 7/2015 | Cunningham | E21B 43/26 |
| | | | 166/281 |
| 2016/0347990 A1* | 12/2016 | Vanzin | C09K 8/602 |
| 2016/0349174 A1* | 12/2016 | Washburn | G01N 33/28 |
| 2018/0313807 A1* | 11/2018 | Michael | G01N 30/7206 |

* cited by examiner

THREE-DIMENSION UNCONVENTIONAL RESERVOIR MONITORING USING HIGH-RESOLUTION GEOCHEMICAL FINGERPRINTING

This application is a continuation of U.S. patent application Ser. No. 16/392,109, filed Apr. 23, 2019, which claims priority to and benefit of U.S. Provisional Applications No. 62/837,119, filed Apr. 22, 2019, No. 62/837,114, filed Apr. 22, 2019, No. 62/671,510, filed May 15, 2018, and No. 62/661,109, filed Apr. 23, 2018, the complete disclosures, specifications, drawings and appendices of which are incorporated herein by specific reference in their entireties for all purposes.

FIELD OF INVENTION

This invention relates to a system and methods for unconventional reservoir monitoring, fracture height determination and evaluation, and cluster efficiency evaluation. More particularly, this invention relates to a system and methods for unconventional reservoir monitoring in three dimensions using high-resolution geochemical fingerprinting analyses.

BACKGROUND OF THE INVENTION

According to the U.S. Energy Information Administration (EIA), crude oil production from unconventional reservoirs accounted for almost 50% of total U.S. crude oil production in 2017. Unconventional reservoirs include reservoirs such as tight sands, gas and oil shales, coalbed methane, heavy oil and tar sands. These reservoirs typically have extremely low permeability (nano-darcy to micro-darcy), and require special recovery operations (such as horizontal drilling and hydraulic fracturing) in order to produce the oil. During a typical hydraulic fracturing treatment, for example, fracturing fluid (primarily water with proppants, such as sands, suspended in it) is pumped downhole into the formation at high pressure to create cracks in the unconventional reservoir. The proppants remain in the fractures after the treatment is completed, and hold the fractures open. The reservoir conductivity is therefore enhanced by the hydraulic fracturing treatment, allowing hydrocarbon flow to the wellbore.

Despite of the effectiveness of hydraulic fracturing and similar treatments in promoting hydrocarbon flow, the industry lacks tools to monitor unconventional reservoir performance after the treatment. Traditional methods such as microseismic imaging and borehole gauges rely on indirect measurements of physics-based parameters (including, but not limited to, acoustic, pressure, and the like) to infer the reservoir performance. Those methods are typically very expensive (i.e., costing multi-millions of dollars), and the results can be unreliable depending on the interpretation methods used.

Examples of prior art methods and system are described in the following references, all of which are incorporated herein by specific reference in their entireties for all purposes:

U.S. Pat. No. 9,074,465 B2, filed Dec. 9, 2009, entitled "Methods for Allocating Commingled Oil Production."

U.S. Pub. No. 2011/0297370, filed May 18, 2011, entitled "Hydrocarbon Production Allocation Methods and Systems."

U.S. Pub. No. 2013/0138360 A1, filed Nov. 30, 2011, entitled "Allocating Oil Production from Geochemical Fingerprints."

U.S. Pub. No. 2014/0250999 A1, filed Mar. 28, 2012, entitled "Method and System for Reservoir Surveillance Utilizing a Clumped Isotope and/or Noble Gas Data."

U.S. Pat. No. 9,638,821 B2, filed Mar. 16, 2015, entitled "Mapping and Monitoring of Hydraulic Fractures using Vector Magnetometers."

U.S. Pub. No. 2017/0260854 A1, filed Sep. 14, 2017, entitled "Hydraulic Fracture Monitoring by Low-frequency DAS."

U S Pub No. 2018/0016890 A1, filed Sep. 25, 2017, entitled "Hydraulic Fracture Analysis."

U.S. Pub No. 2018/0313807 A1, filed Apr. 26, 2018, entitled "Time-series Geochemisty in Unconventional Plays"

Bennett, B. et al, 2009, Oil Fingerprinting for Production Allocation. Exploring the Natural Variations in Fluid Properties Encountered in Heavy Oil and Oil Sand Reservoirs, 2009 CSPG CSEF CWLS Convention, Calgary, Alberta, Canada.

Elsinger R. J., et al., 2010, Otter-Eider Geochemical Production Allocation: 6+ Years of Continuous Monitoring to Provide Fiscal Measurements for Hydrocarbon Accounting, AAPG Hedberg Conference, Vail, Colo., Jun. 8-11, 2010.

Rasdi, F. et al. 2012, An Investigation of Vertical and Lateral Communication in an Unconventional Oil Reservoir Using Geochemistry and Reservoir Simulation, SPE Canadian Unconventional Resources Conference, Oct. 30-Nov. 1, 2012, Calgary, Alberta, Canada.

Nouvelle, X., et al., 2012, Novel Method of Production Back-Allocation Using Geochemical Fingerprinting, the Abu Dhabi International Petroleum Exhibition & Conference, Abu Dhabi, UAE, Nov. 11-14, 2012.

Lareau, H. et al., 2016, Utilizing Geochemical Analysis in Unconventional Reservoirs to Allocate Produced Oils to Stratigraphic Zone, AAPG/SEG International Conference and Exhibition, April 3-6, Barcelona, Spain.

Huong, H. T., et al., 2017, Application of Geochemical Technique to Reduce Allocation Cost for Commingled Production Wells from Multiple Reservoirs, Petrvietnam Journal, vol. 10, p 45-50.

Jweda, J. et al., 2017, Optimizing Field Development Strategy using Time-lapse Geochemistry in Eagle Ford, Unconventional Resources Technology Conference, Jul. 24-26, 2017, Austin, Tex.

Liu, F., et al., 2017, Time-lapse Geochemistry (TLG) Application in Unconventional Reservoir Development, Unconventional Resources Technology Conference, Jul. 24-26, 2017, Austin, Tex.

Huang, R., J. et al, 2000, Allocation of Commingled Pipeline Oils to Field Production, Organic Geochemistry, v. 31, p 1463-1474.

Kaufman, R. L., et al. 1987, A New Technique for the Analysis of Commingled Oils and Its Application to Production Allocation Calculations, $16^{th}$ Annual Indonesian Petro. Assoc, IPA 87-23/21, p 247-268.

Kaufman, R. L., et al., 1990, Gas Chromatography as a Development and Production Tool for Fingerprint Oils from Individual Reservoirs: Applications in the Gulf of Mexico, Proceedings of the $9^{th}$ Annual Research Conference of the Society of Economic Paleotologists, and Mineralogists, New Orleans, p 263-282

McCaffrey, M. A., et al, 1996, Using Biomarkers to Improve Heavy Oil Reservoir Management: An Example from the Cymric Field, Kern County, Calif., AAPG Bulletin, v. 80, p 904-919.

Peters, K., et al., 2008, De-convoluting Mixed Crude Oil in Prudhoe Bay Field, North Slope, Ak., Organic Geochemistry, v. 39, p 623-645.

McCaffrey, M. A., et al., 2012, Oil Fingerprinting Dramatically Reduces Production Allocation Costs, World Oil, March 2012, p 55-59.

Baskin, D. K., et a, 2014, Allocation the Contribution of Oil from the Eagle Ford Formation, the Buda Formation, and Austin Chalk to Commingled Production from Horizontal Wells in South Tex. Using Geochemical Fingerprinting Technology, AAPG Annual Conventional, May 19-23, 2013, Search and Discovery Article #41268.

McCaffrey, M. A., et al., 2011, Geochemical Allocation of Commingled Oil Production or Cominged Gas Production, SPE Western North American Regional Meeting, May 7-11, 2011, Anchorage, Ak., USA.

McCaffrey, M. A., el al., 2016, Applying Oil Fingerprinting to Unconventional Reservoirs in the Permian Basin for Characterization of Frac Height and Quantification of the Contribution of Multiple Formations to Commingled Production, Unconventional Resources Technology Conference (URTec), Aug. 1-3, 2016, San Antonio, Tex., USA.

Geochemical fingerprinting provides a more direct method to monitor a reservoir through information collected directly from the produced oil and/or oil extracted from rock samples, and has some application in monitoring conventional reservoir production, as described above. However, there is a need in the art for such methods and systems using geochemical fingerprinting that provide monitoring of the unconventional reservoir in all three dimensions. In this manner, the unconventional reservoir development plan may be adjusted to improve reservoir economics and reduce environmental impacts.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein.

DETAILED DESCRIPTION OF EXEMPLARY EMBODIMENTS

In various exemplary embodiments, the present invention comprises methods and systems using geochemical fingerprinting to provide monitoring of an unconventional reservoir in all three dimensions.

As used herein, a "reservoir" is a geological formation or a portion of a formation that includes sufficient porosity and permeability to store and transmit fluid, primarily oil.

As used herein, a "rock sample" can be either a core sample or cutting sample. "Core" is a sample of rock in cylinder shape retrieved from the side of a drilled oil and gas well. It can be either a whole core which is typically in 4 inch diameter, or a side-wall core which is typically in 1 inch diameter. "Cuttings" are the broken pieces of rock chips generated during drilling and returned to the surface with drilling mud.

As used herein, a "end member" (or end-member) in mineralogy is a mineral that is at the extreme end of a mineral series in terms of purity. In this context, it refers to oil that originates from a completely separate zone and thus carries distinct geochemical signatures. It is in contrast to commingled oil which is a mixture of oils produced from various zones, or a mixture of end member oils.

As used herein, "geochemical fingerprint" is an analysis of the chemical and/or isotopic signatures of an oil or rock sample and is typically complex and unique enough to distinguish samples from each other.

As used herein, GC×GC (also 2D comprehensive GC×GC or 2DGC) is comprehensive two-dimensional gas chromatography where all analyte that enters the $1^{st}$ column gets partitioned using a modulator to pass through the $2^{nd}$ dimension column to the same detector.

As used herein, "production allocation" is a technique to allocate produced oil back to its sourcing geological intervals based on geochemical fingerprint data collected from oil and rock samples.

"Blob" as commonly used in comprehensive two-dimensional gas chromatography (or GC×GC), and "peak" as commonly used in one dimensional gas chromatogram (or GC), all refer to separated chemical compounds in a chromatogram, and are used interchangeably herein.

Figure 1:
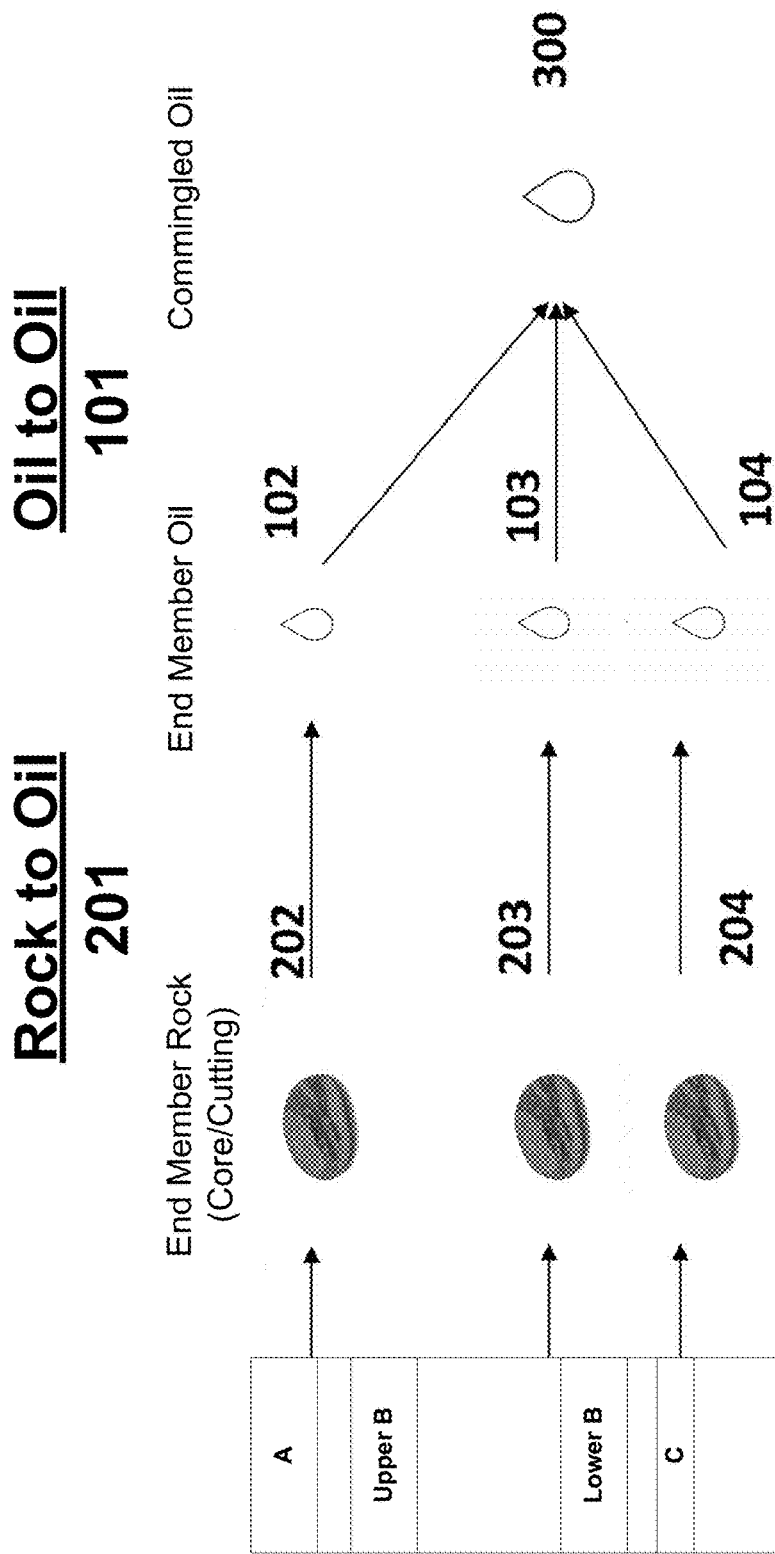
FIG. 1 shows a conceptual diagram of geochemical fingerprint-based production allocation.

In various exemplary embodiments, the present invention comprises an improved method of using geochemical fingerprint information to allocate produced oil back to subsurface contributing zones (i.e., "oil to oil production allocation" 101) for monitoring unconventional reservoir production, as seen in FIG. 1. For conventional allocation for conventional reservoirs, representative end member samples of produced oil 102, 103, 104 are collected from each contributing zone, and geochemical fingerprints are measured for each of the end member oils, which are then collected and compared to geochemical fingerprints from the produced, commingled oil 300. A linear regression model is then built for the produced oil samples based on either the geochemical compound peak or peak ratios, which is then used to back-calculate the percentage of contribution from each zone represented by the end member oils.

However, this methodology is not applicable for unconventional reservoirs (such as shale reservoirs and heavy oil sands) due to the difficulty of acquiring representative end member oil samples, as well as the high degree of similarity in geochemical fingerprint information between contributing zones. Chemical extraction of oil from representative rock samples 202, 203, 204 as pseudo end-members may be accomplished using various solvents (e.g., dichloromethane, toluene, pentane, carbon disulfide) as a form of "rock to oil production allocation." 201. However, the inherent fractionation between chemically extracted oil from rock and naturally produced oil still limits the scope of production allocation for unconventional reservoirs, causing prior art methods of production allocation to require a location identifier for each of the end member samples. The process of providing the location identifier for each end members significantly reduces the robustness of the model prediction, and location identifier information often is not always available, further limiting the scope of previous production allocation methods in unconventional reservoirs. The physical extraction method (as described in U.S. Provisional Application No. 62/661,109) fundamentally solves this problem, so that oil extracted using the physical extraction method is much more similar to the produced oil, thereby making "rock to oil" production allocation feasible.

In addition, crude oil consists of thousands of naturally occurring compounds, but the traditional one-dimensional gas chromatography is statistically limited in case of mixtures exceeding 50 to 60 compounds. Finally, due to the presence of both horizontal and vertical well-bores in unconventional reservoirs, there is a need to monitoring reservoir production not only vertically from various contributing zones or geological formations, but also horizontally or laterally from different stages of clusters to determine cluster efficiency and other parameters.

In various exemplary embodiments, the present invention has the following advantages: (1) end members are established using physically extracted oil from corresponding rock samples; (2) geochemical fingerprint data for both rock samples and produced oil samples is obtained using multidimensional (such as two-dimensional) gas chromatography and preprocessed through steps of peak detection, integration and alignment specifically designed for crude oil GCGC data, resulting in an order-of-magnitude higher compound resolution (typically over 2000 compounds resolved) than prior art one-dimensional gas chromatography (typically fewer than 100 compounds resolved), in subsequent significant expansion in the applicability of production allocation in reservoirs that are highly similar, and in improved production allocation accuracy; (3) production allocation is conducted both vertically and horizontally, allowing production efficiency evaluation along the horizontal well; and (4) there is no need to assign location and/or time identifiers to samples, expanding the scope of applicability where location/time identifier information is not available and increasing the robustness of the production allocation method. The geochemical fingerprint based production allocation described herein thus provides an effective, inexpensive and flexible way to monitor unconventional reservoir production both vertically and laterally. It may be used to optimize well stacking and spacing, completion design, and cluster efficiency evaluation, thereby improving unconventional reservoir economics.

Figure 2:
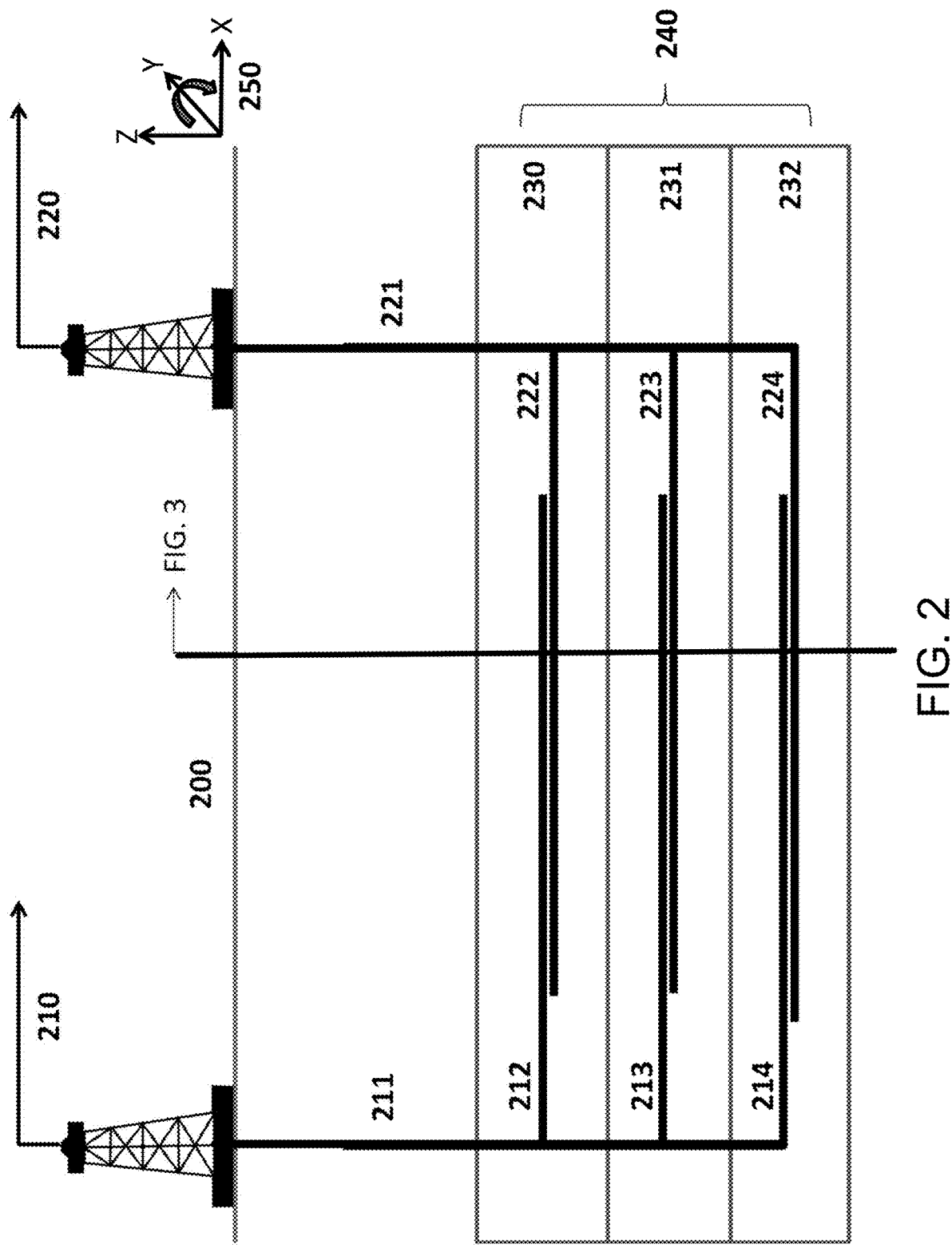
FIG. 2 illustrates a cross-section view of a subterranean unconventional reservoir development with a plurality of horizontal wells stacked both vertically and horizontally, the cross-section view parallel to the direction of the horizontal wellbores.
Figure 3:
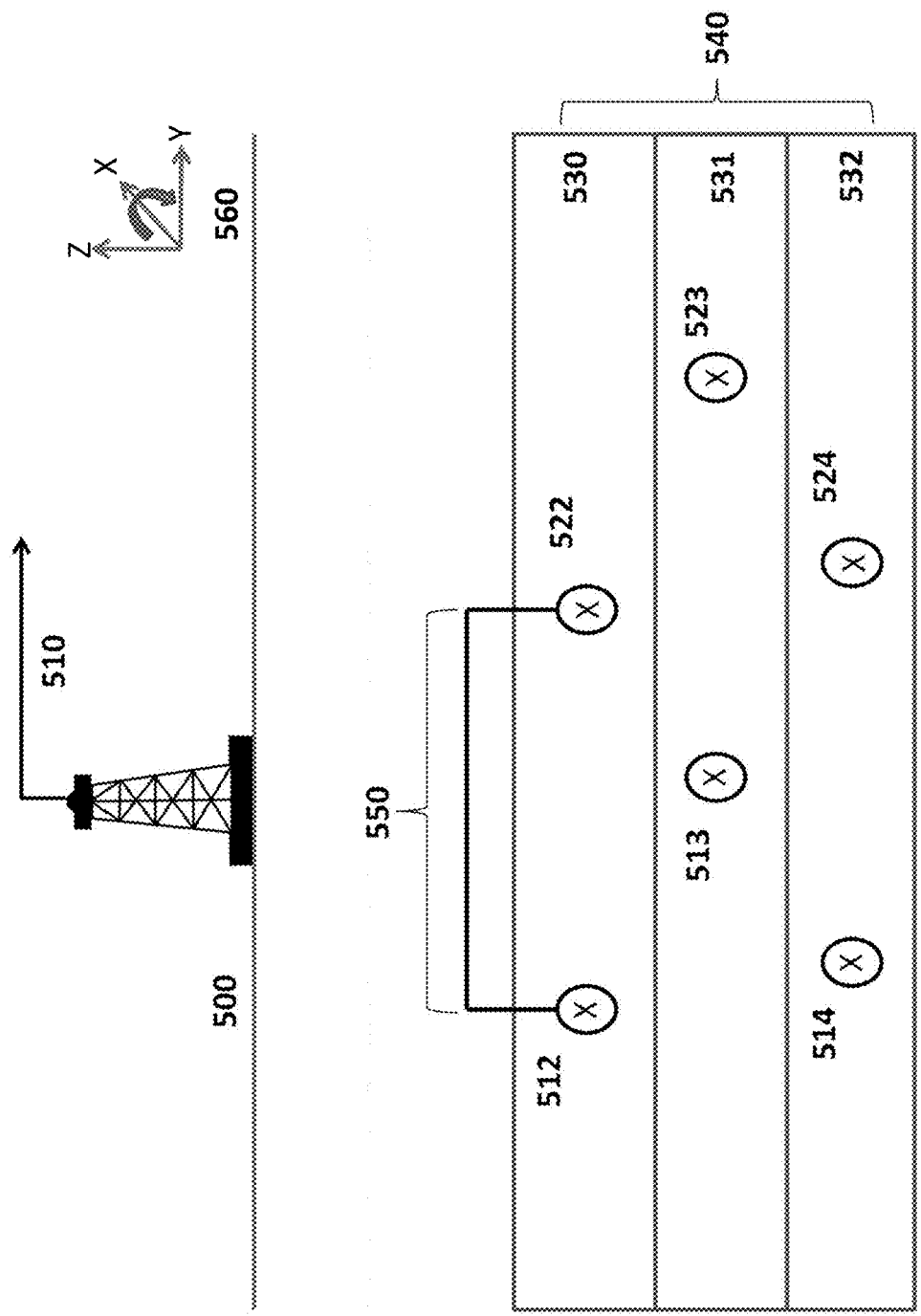
FIG. 3 illustrates a cross-section view of a subterranean unconventional reservoir development with a plurality of horizontal wells stacked both vertically and horizontally, the cross-section view perpendicular to the direction of the horizontal wellbores.

A subterranean unconventional reservoir is often developed through a plurality of horizontal wells stacked both vertically and horizontally, as seen in FIGS. 2 and 3. FIG. 1 shows a cross-sectional view parallel to the general direction of the horizontal wells (in Cartesian coordinates 250, the X-Z plane). Here, six horizontal wells are producing hydrocarbon from the unconventional reservoir 240 through two surface well pads 210 and 220. Horizontal wells 212, 213, and 214 produce oil to the surface 200 through well pad 210, and horizontal wells 222, 223, and 224 produce oil to the surface 200 through well pad 220. In unconventional reservoir development planning, the reservoir is typically further divided into multiple horizontal development zones where multiple layers of horizontal wells can be drilled to extract hydrocarbon to the surface 200 effectively. The division of the horizontal zones can be completely artificial with no geological constraints, or based on geological variation between the zones or impermeable barriers in between. In the current example, the unconventional reservoir 240 is further divided into three horizontal development zones 230, 231, 232. The horizontal wells 212 and 222 are drilled in zone 230, wells 213 and 223 in zone 231, and wells 214 and 224 in zone 232.

FIG. 3 illustrates a cross-section of the reservoir of FIG. 2 in the direction perpendicular to the general direction of the horizontal wells (the Y-Z plane, in Cartesian coordinates 360). The lateral spacing between the horizontal wells in the same zone (e.g. the lateral distance 350 between wells 212 and 222 in zone 230, or wells 213 and 223 in zone 231, or wells 214 and 224 in zone 332) can be anywhere from a few hundred feet to a few thousand feet, and can differ between zones as well.

Although the example shown demonstrates three horizontal development zones in an unconventional reservoir with two horizontal wells placed in each zone, a person of ordinary skill in the art will recognize that the methods herein may be applied to any number of horizontal development zones and any number of horizontal well placements in a zone.

Figure 4:
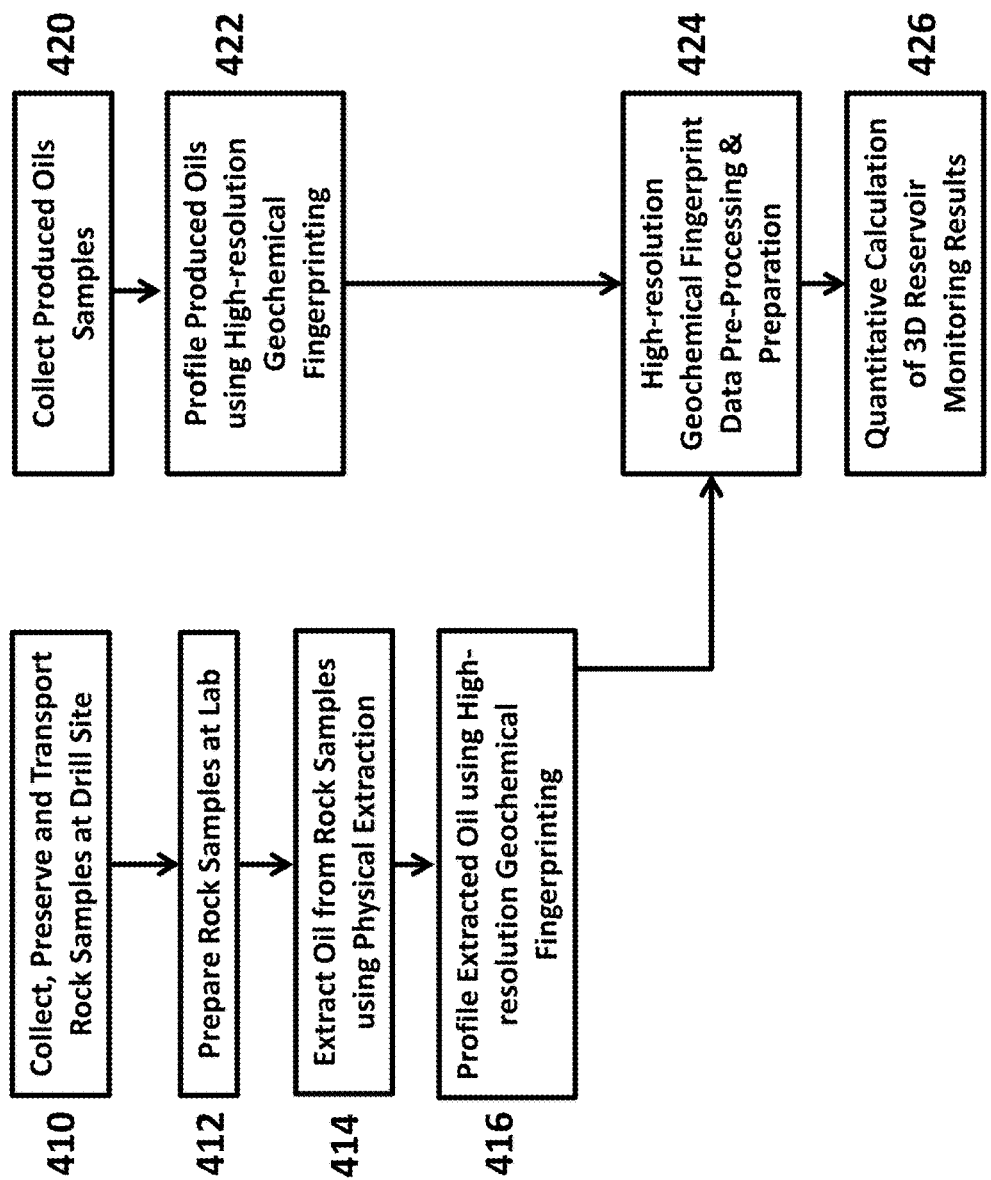
FIG. 4 is a chart showing method steps for 3D unconventional reservoir monitoring using high-resolution geochemical fingerprinting method, according to an exemplary embodiment of the present invention.
Figure 5:
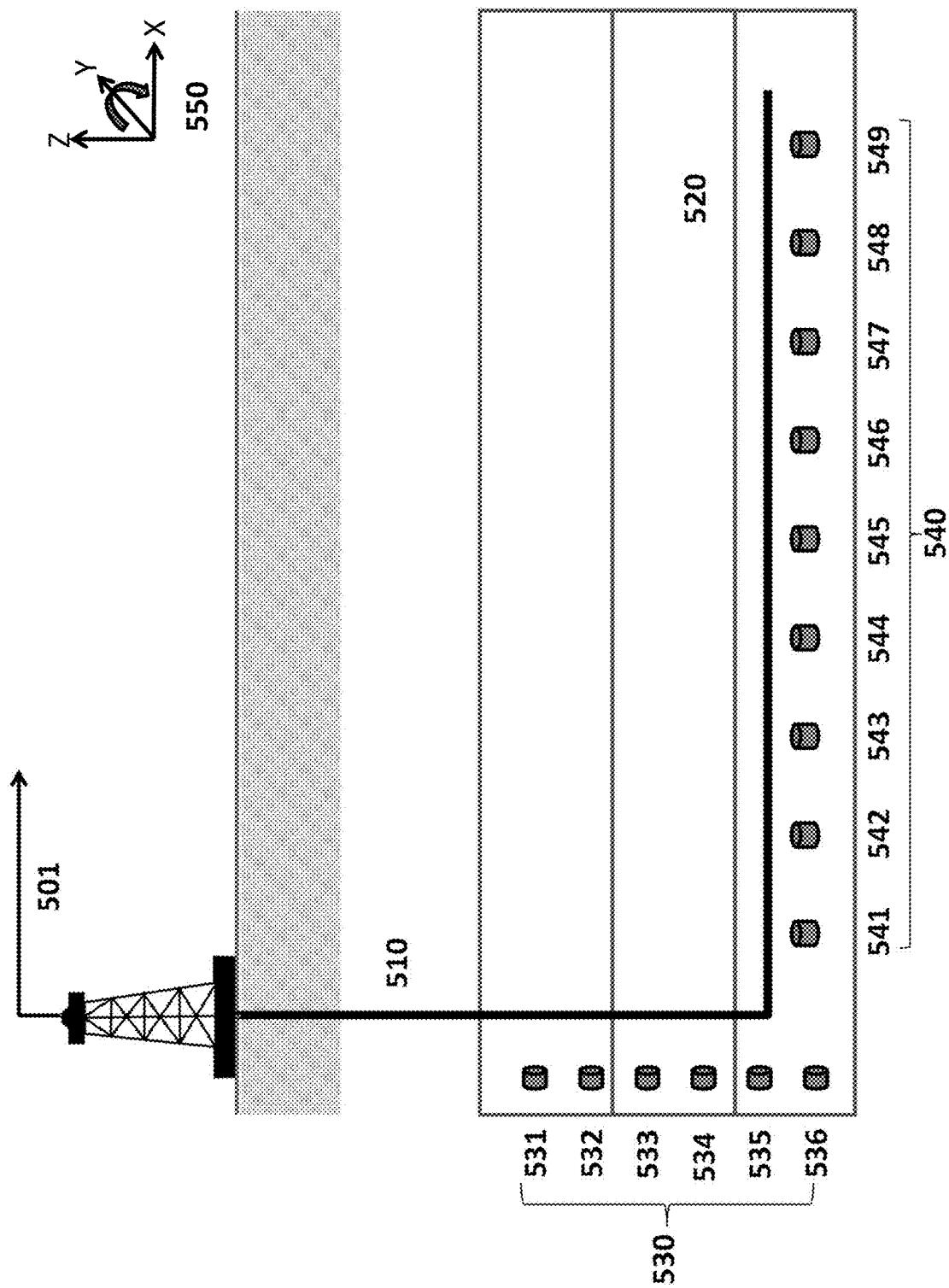
FIG. 5 illustrates the positioning of cutting samples collection in both the vertical and horizontal part of a well.

FIG. 4 is a flowchart showing steps in an exemplary embodiment of the 3D unconventional reservoir monitoring process using high-resolution geochemical fingerprinting. In step 410, rock samples, either drill core or cuttings, are collected and preserved on-site during the drilling. The preservation methods may include sealing in glass jar, dry-icing, and pressurized cell for sample preservation and transportation, as described in U.S. Provisional Application No. 62/661,109, filed Apr. 23, 2018. Rock samples are collected both on the vertical part 530 and the horizontal part 540 of the well, as shown in FIG. 5. These rock samples serve as end-members for step 414. The intervals between each cutting collection for the vertical end-members (samples 531 to 536) are typically between approximately 10 to approximately 50 feet depending on the requirement of monitoring accuracy vertically and the availability of the samples. The sampling intervals along the lateral end-members (samples 541 to 549) are typically wider between approximately 200 to approximately 500 feet because of less geological heterogeneity laterally than vertically.

The rock samples collected on the vertical part 540 serve as end-members to monitor the reservoir 240 in the Z-axis direction. The cutting samples collected on the horizontal part 440 serve as end-members to monitor the reservoir 240 in the X-axis direction. And produced oil samples and/or rock samples from different horizontal wells drilled in the same horizontal zone (e.g., wells 212 and 222) serve as end-members to monitor the reservoir 240 in the Y-axis direction.

Although the example described herein sampled all six wells in order to provide comprehensive three-dimensional monitoring results of the unconventional reservoir, the methods herein may be applied to any number of wells to provide monitoring results in any of the X, Y, or Z-axis directions of interest by selecting the proper sample end-members.

In step 412, rock samples are transported to the laboratory in a sealed container (such as an isojar) and prepared for geochemical analysis Cutting samples are cleaned using water-based solution for multiple times, dried, and ground to 20 to 100 mesh size. The water-based solution may be consisted of sodium chloride, potassium chloride, and other components. If core samples are used, the interior piece of a core is sampled, ground to 20 to 100 mesh size.

Figure 6:
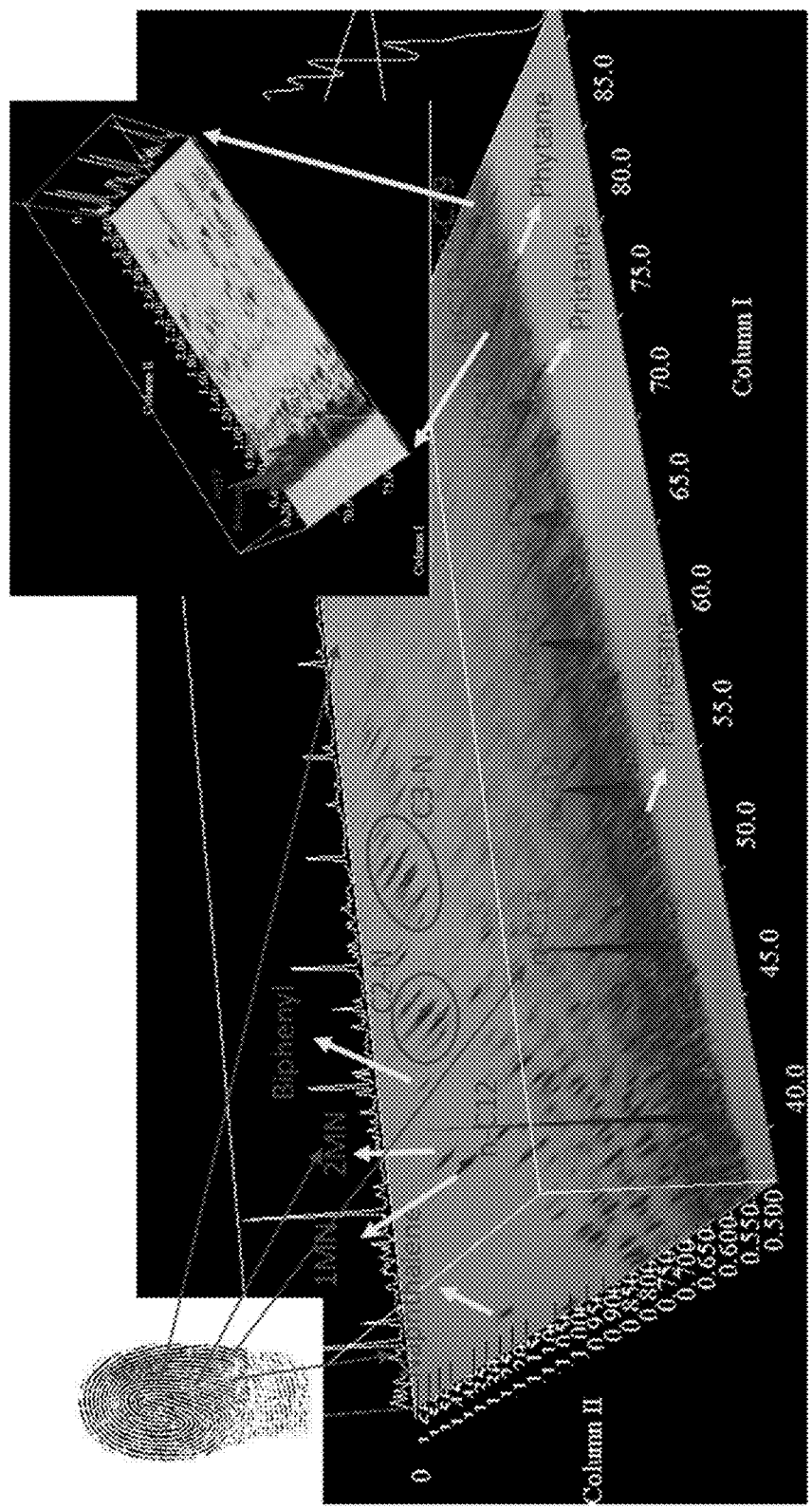
FIG. 6 is an example of a 3D view of a GC×GC chromatogram collected from a rock sample using physical extraction.

In step 414, oil from the prepared rock samples is extracted using physical extraction methods, such as those described in U.S. Provisional Application No. 62/661,109, filed Apr. 23, 2018, to avoid light hydrocarbon loss and to avoid complications due to organic solvents that are typically used during standard processes for oil extraction from rock. The extracted oil is then analyzed in step 416 by any methods or combinations of methods that are capable of providing high-resolution geochemical fingerprints. Those methods include, but not limited to, comprehensive two-dimensional gas chromatography with flame ionization detector (GC×GC-FID) (an example of extracted geochemical fingerprint data from rock sample is seen in FIG. 6), comprehensive two-dimensional gas chromatography with mass spectrometry (GC×GC-MS), comprehensive two-dimensional liquid chromatography (LC×LC), gas chromatography with isotope ratio mass spectrometry (GC-IRMS), excitation-emission matrix (EEM) fluorescence spectrometry, and electromagnetic scattering spectroscopic measurement such as Ramen spectroscopy. In step 420, produced oil samples are collected from the multiple horizontal wells of interest drilled in the same unconventional reservoir. An example is given in FIG. 3 where produced oil are collected from six horizontal wells (well 212, 213, 214, 222, 223, and 224) drilled in the same unconventional reservoir 240. Collection of produced oil samples can be repeated a plurality of times to provide monitoring results at any time of interest during production.

Figure 7:
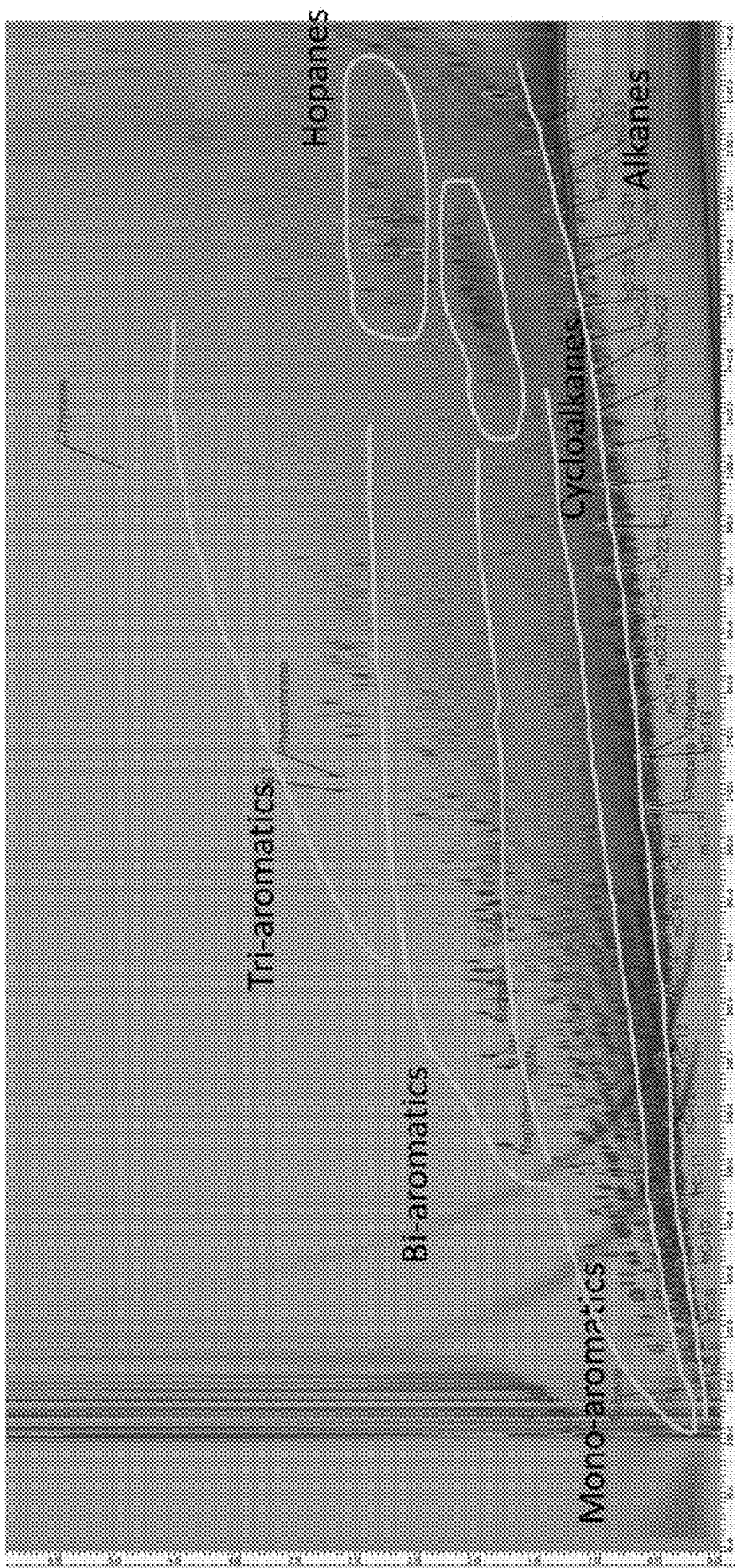
FIG. 7 is an example of top-view of a GC×GC chromatogram collected from a produced oil sample using physical extraction.

In step 422, produced oil samples are profiled using methods as described in step 416 (an example of extracted geochemical fingerprint data from produced oil sample is shown in FIG. 7).

In step 424, the high-resolution geochemical fingerprint data from rock samples (step 416) and produced oil samples (step 422) are pre-processed and prepared to generate a selection of clean and meaningful dataset to present each of the rock and produced oil sample. The geochemical fingerprint data pre-processing may involve various additional steps (e.g. baseline removal, noise attenuation, peak detection, integration, and alignment) based on the nature of the geochemical fingerprint data.

Figure 8:
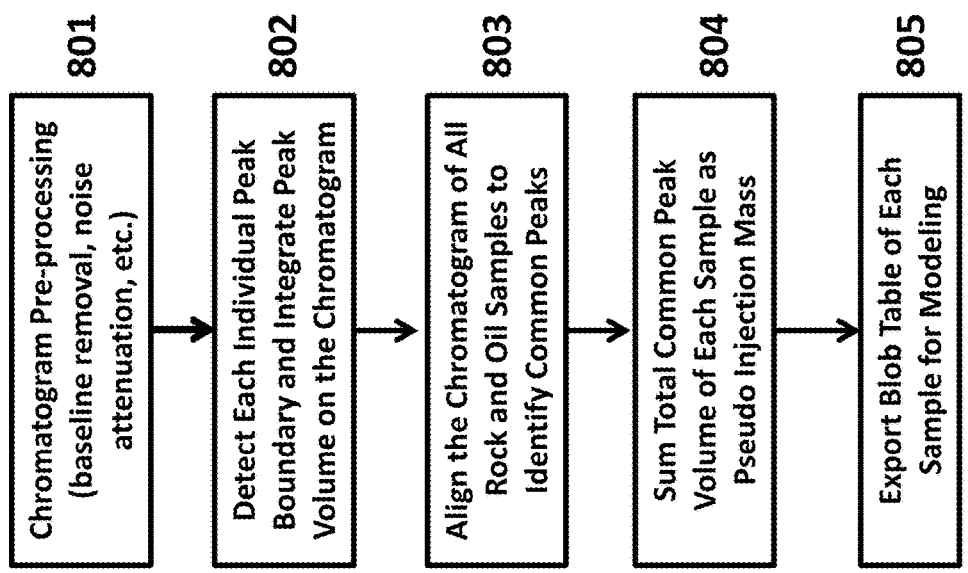
FIG. 8 is a chart showing method steps for geochemical fingerprint GC×GC data pre-processing and preparation.

A typical workflow involved in step 424 is illustrated in FIG. 8. For example, in pre-processing GC×GC data 801, the raw geochemical data collected from the instruments are just millions of data points consisting of intensity data vs. retention time. Different chemical compounds in the oil or rock samples are separated by the GC×GC through both the $1^{st}$ and $2^{nd}$ columns due to their unique chemical properties, and are detected at the detector, generating what are called "peaks." Therefore, a peak recorded in a raw chromatogram needs to be detected properly and its volume integrated 802 to quantify the mass of each compound that it is representing. "Peak detection" means detecting the boundary (in 2D)) or the contour (in 3D) of a peak so that the volume within the detected contours can be integrated to represent the compound mass. This step is essentially translating the raw geochemical data detected from the instruments into numerical data sets representing the geochemical information carried in each oil or rock sample There are thousands of naturally-occurring compounds existing in crude oil leading to an order of magnitude more compounds in a GC×GC chromatogram. Prior art peak detection methods similar data cannot not properly handle large number of peaks, leading to erroneous peak detection in crude oil samples, as illustrated by the darker contours in FIG. 9. The present in invention is specifically designed to handle large amount of peaks (typically thousands) that elute very close to each other in a chromatogram, thereby generating more precise and accurate blob contours, as illustrated by the lighter contours in FIG. 9. Since the entire production allocation calculation is built based on the compound mass information by integrating the detected peak, the present inventive peak detection method is crucial to improve the accuracy of the production allocation method.

Figure 9:
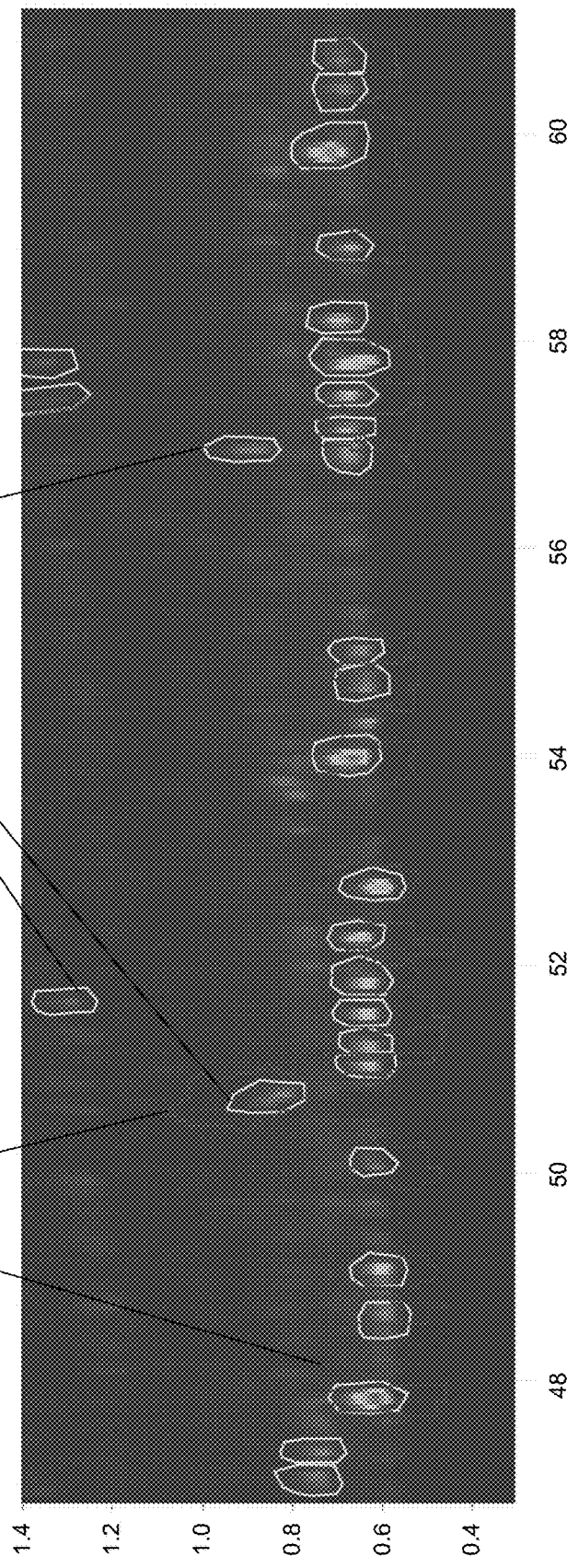
FIG. 9 is an example illustrating the peak detection process of GC×GC data.

An example of the peak detection process of GC×GC data 802 is illustrated in FIG. 9. After all peaks are detected for each chromatogram, the same peak representing the same compound needs to be aligned 803 among all the samples so the peak values of different samples can be compared. Since there are well over 2000 compounds resolved in a typical crude oil GC×GC and there are only approximately 50 to 60 compounds that are known to human knowledge, the rest of the over 1000 compounds need to be each given a "pseudo peak ID" so that they can be compared among different samples without knowing each specific compound identification. This process of assigning "pseudo peak ID" to peaks representing the same compound among different chromatogram is called "peak alignment" 803.

Figure 10:
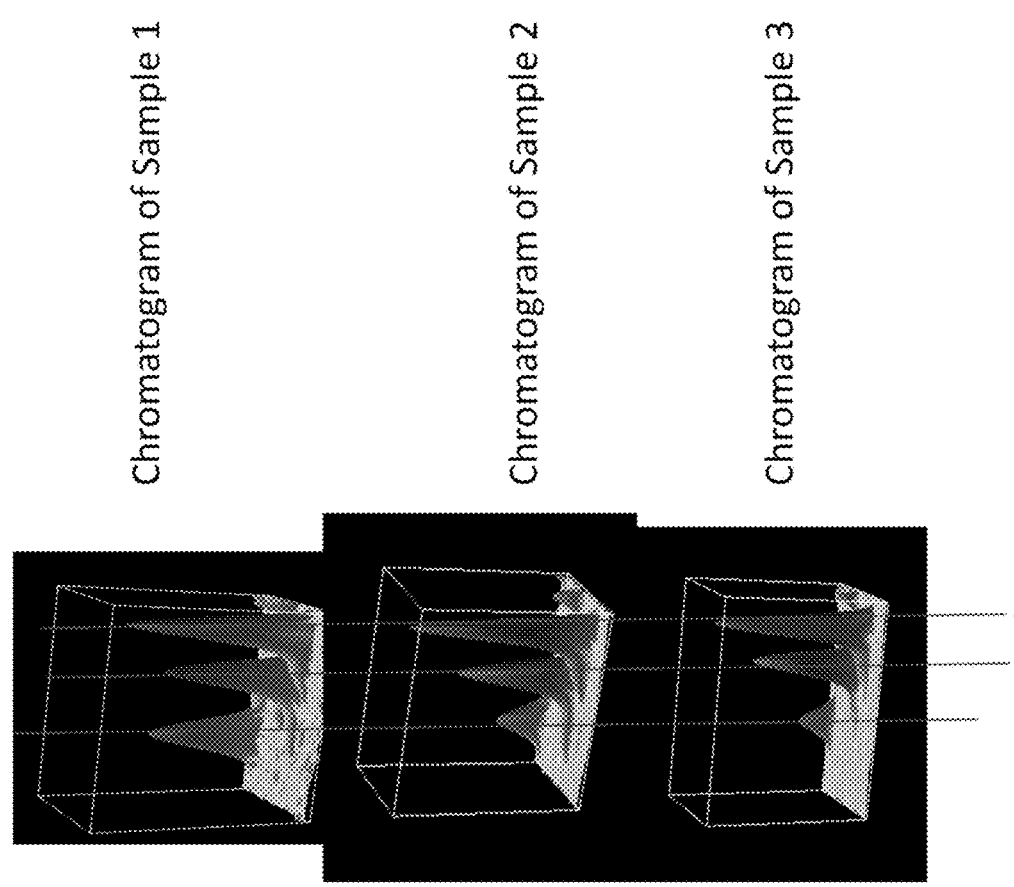
FIG. 10 is an example illustrating the process of peak alignment of GC×GC data.

An example of the peak alignment process among different GC×GC data of crude oil samples 803 is shown in FIG. 10. The peak volumes of all the detected peaks from each chromatogram are then added together to be used in the following calculations as pseudo injection mass of the sample 804. All the detected peaks are exported into a "blob table" 805 which includes key information of chromatogram needed for modeling in 426 including, but not limited to, peak retention time I, peak retention time 11, and integrated peak volume.

Additionally, quality control may be done by repeating measurements on the same sample multiple times, and the data that are not consistent between those repeat runs are removed. In other cases, only part of the signal is used so as to focus on the most differentiating part of the signal reflecting, for instance, a certain fraction of the oils (e.g., the $C_2$-naphthelene fraction of the oil revealed by 2D comprehensive GC×GC analysis, as seen in FIG. 7). In some embodiments, a multivariate analysis technique such as principal component analysis (PCA) and clustering analysis is used to select the most differentiating features in the dataset. In other embodiments, the data is further cleaned by ways of retention time shift correction, signal scale correction and alignment, and the like, to limit errors/uncertainties, while making the data easily comparable. In further additional embodiments, the derivative of the signal is used to enhance the features of the signal using techniques such as Fourier/wavelet transform, image deconvolution, and the like.

The end result of step 424 is a selection of a clean and meaningful dataset representing each of the rock and oil samples. Those dataset is used to build the model(s) in step 426 to allocate each produced oil sample back to its sourcing formations, which are represented by the rock samples. This process is also called production allocation. It is essentially an inverse problem and various techniques can be used to solve this inverse problem. The most classic method is to build a regression model using the rock samples as end members and the produced oil samples as the target. Such a calculation is performed using linear least-squares, singular value decomposition, or any optimization process. The system to solve is G·x=d, where G is the it by m matrix constituted of end-members data, x is the in-vector with proportion of each end-member, and d is the n-vector constituted of the data measured of produced oil. The input data can be either the original geochemical fingerprint data, or any format of transformed dataset of the geochemical fingerprint data including derivatives, deconvolution values, singular decomposition values, and the like.

For example, for a simple two end member production allocation problem: based on the principle of gas chromatography, for a given compound A, its concentration for any given compound A, its concentration $$(x_{RM1}^A)$$

in the injected oil (e.g. the end member 1, or EM1) equals to the corresponding GC peak volume $$(V_{RM1}^A)$$

times response factor $\gamma\_A$.

$$\text{In } EM\ 1,\ x_{EM1}^A = \frac{V_{EM1}^A \cdot \gamma_A}{M_{EM1}^{[n]}}$$

$$\text{In } EM\ 2,\ x_{EM2}^A = \frac{V_{EM2}^A \cdot \gamma_A}{M_{EM2}^{[n]}}$$

In the mixture which is the produced oil M1, based on mass balance, the concentration of A in the $$(x_{M1}^A),$$

equals the concentration of A in EM 1

$$(x_{EM1}^A)$$

times its mixing ratio (R1) in M1 plus the same thing in M2

$$x_{M1}^A = x_{EM1}^A \cdot R_1 + x_{EM2}^A \cdot R_2$$

For the same compound, response factor $\gamma A$ is the same and can cancel out. The concentration of compound A is known from integrating its corresponding peak in the chromatogram and quantify by using internal standard. And the injection mass can be calculated from the GC×GC data by integrating all the peaks in the chromatogram and quantify by using internal standard. Since R1 and R2 add up to 100%, there is only one unknown in the above equation which is R1 The equation can therefore be solved. For system with more end members, more compounds need to be used to establish multiple equations.

Another method to conduct production allocation in step 426 is to train the machine to make prediction on the mixing ratios using known production allocation results from previous studies, i.e. using a machine learning technique.

When produced oil samples are collected multiple times from a single well through its production, the time-series quantitative production allocation results can be used as a tool to monitor the single well performance through production. The production allocation results can also be used by the engineers to calibrate reservoir model and frac model to provide decision-makers on oil field development with improved prediction results. When produced oil samples are collected through time from multiple wells in an oil field, the quantitative production allocation results provide an effective monitoring of the performance of the entire oil field including inter-well communications and production sharing.

Figure 11A:
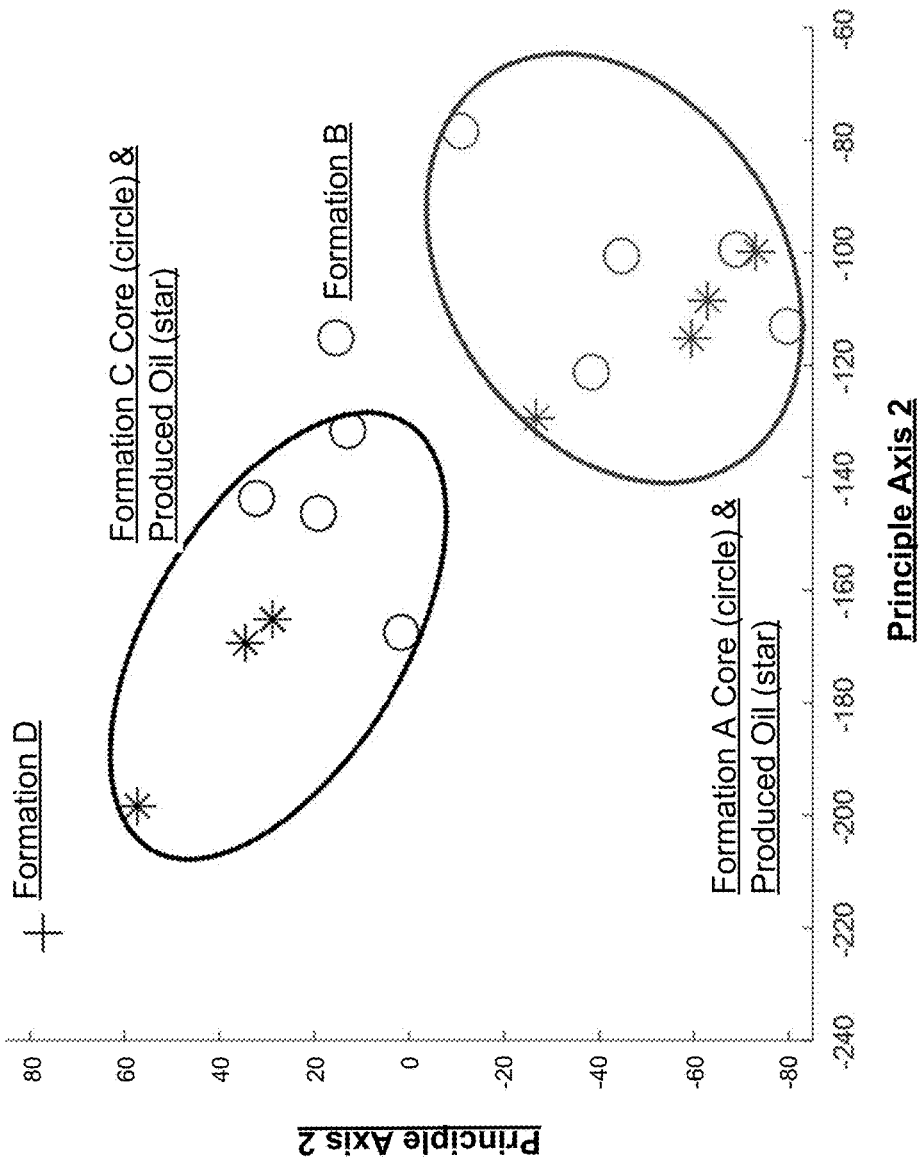
FIGS. 11A and 11B show a comparison of principal component analysis of geochemical fingerprints collected from rock samples using physical extraction (A) vs. chemical extraction (B).
Figure 11B:
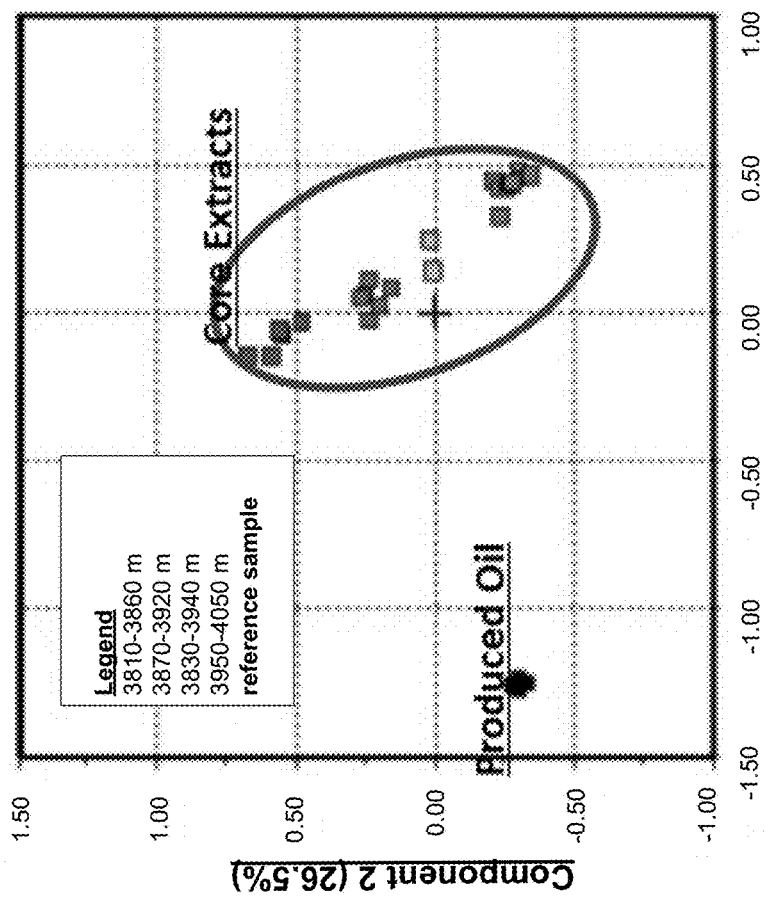
Figure 12:
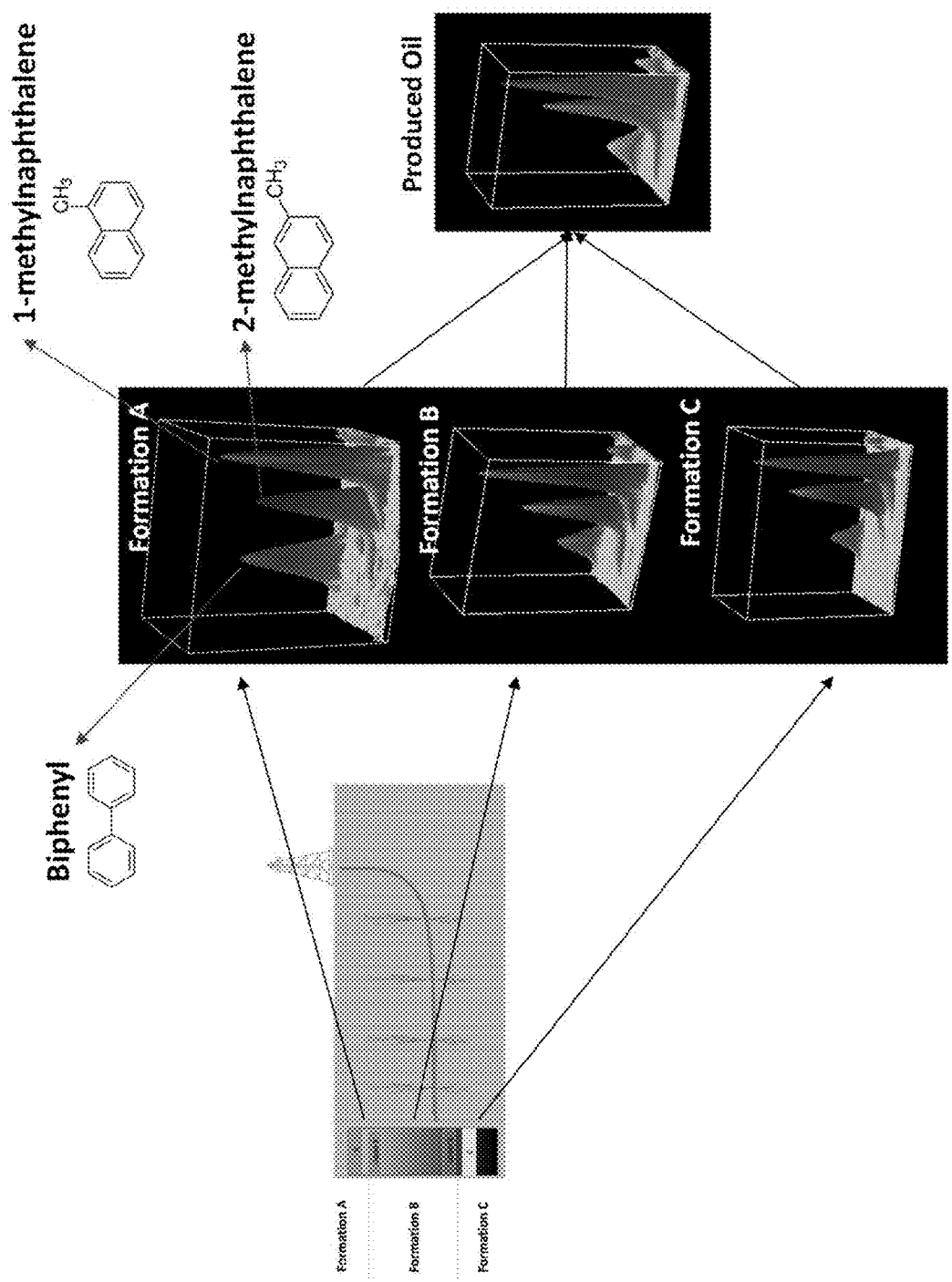
FIG. 12 is geochemical fingerprint collected using physical extraction and GC×GC-FID using cutting samples showing the variation between different formations.

Non-limiting examples of the above-described methods, systems, and devices are provided below:

Example 1—Use of the Method to Monitor Frac Height and Production Allocation in an Unconventional Reservoir Performance in West Texas The following description provides an example of an unconventional reservoir in West Texas, USA. Cutting samples of approximately 50 grams each (half-cup minimum) were collected every 30 feet throughout the interval of interest on the drill site. The cutting samples were rapidly rinsed using tap water, and sealed in isojars to ship to the laboratory. Each cutting sample was sifted to remove the dust, and about 30 grams of each sample was cleaned in the laboratory using de-ionized water 5 times, centrifuged using 1000×g for 1 minute, and air-dried under the fume-hood for 18 hours. The cleaned, dried cutting samples were grounded and sifted down to 40-80 mesh size. Approximately 0.1 gram of prepared sample was loaded to the physical extraction instrument (as described in U.S. Provisional Application No. 62/661,109) and the extractant was measured using GC×GC-FID (Shimadzu GC2030 equipped with Zoex II thermal modulator). Compared to the traditional chemical extraction method where various solvents are used to extract the oil from the rock, physical extraction provides a much superior solution because oil that is physically extracted oil from the rock sample proves to be very similar to the produced oil (as seen in FIG. 11A), in sharp contrast to chemically extracted oil which is substantially different from produced oil (as seen in FIG. 11B), thereby making "rock to oil" production allocation feasible. A geochemical profile was established using geochemical fingerprint data extracted from those vertical cutting samples that effectively differentiated different geological formations through different relative compositions (as seen FIG. 12).

Figure 13:
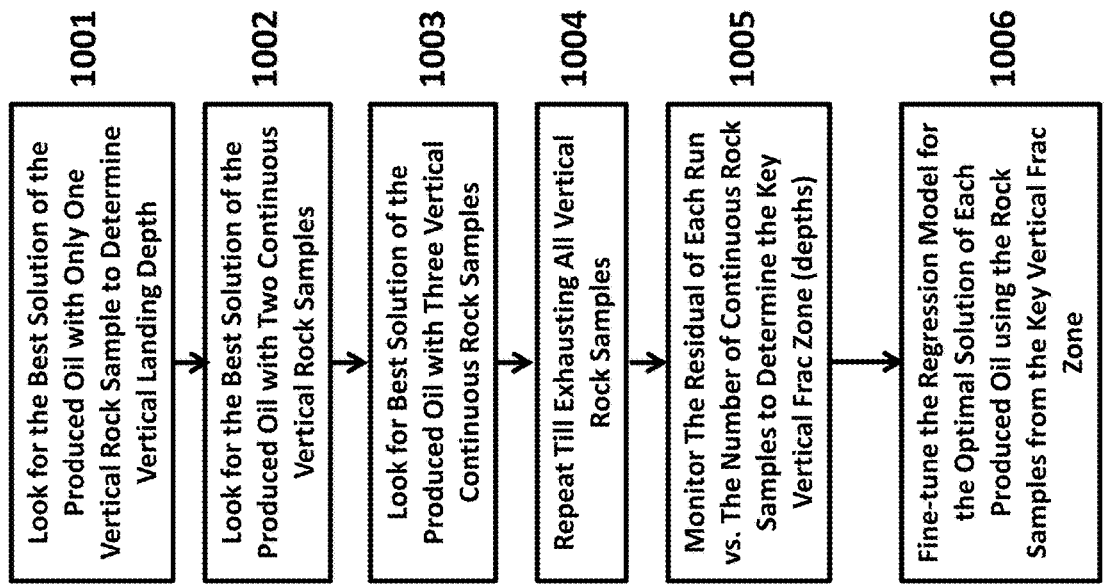
FIG. 13 is a chart showing method steps for vertical fracture height determination and production allocation model.

In this example, produced oil from two wells (A-2 and B-2, locations shown in FIG. 16) were collected over time, and the produced oil samples geochemical fingerprint data were collected using GC×GC-FID (Shimadzu GC2030 equipped with Zoex II thermal modulator). A regression model was built using the vertical cutting samples as end members to back-allocate the produced oil back to its sourcing formations. The process to evaluate the frac height and select end member cutting samples to be used for the regression model is illustrated in FIG. 13:

a. Look for the best solution of the produced oil with only one vertical rock sample to determine vertical landing depth 1001.

b. Look for the best solution of the produced oil with two continuous vertical rock samples 1002.

c. Look for the best solution of the produced oil with three continuous vertical rock samples 1003.

d. Repeat above steps until exhausting all vertical rock samples 1004.

e. Monitor the residual of each run vs. the number of continuous vertical rock samples to determine the key vertical frac zones (depths) 1005.

f. Fine time the regression model for the optimal solution of each produced oil sample using the rock samples from the key vertical frac zone 1006.

Figure 14:
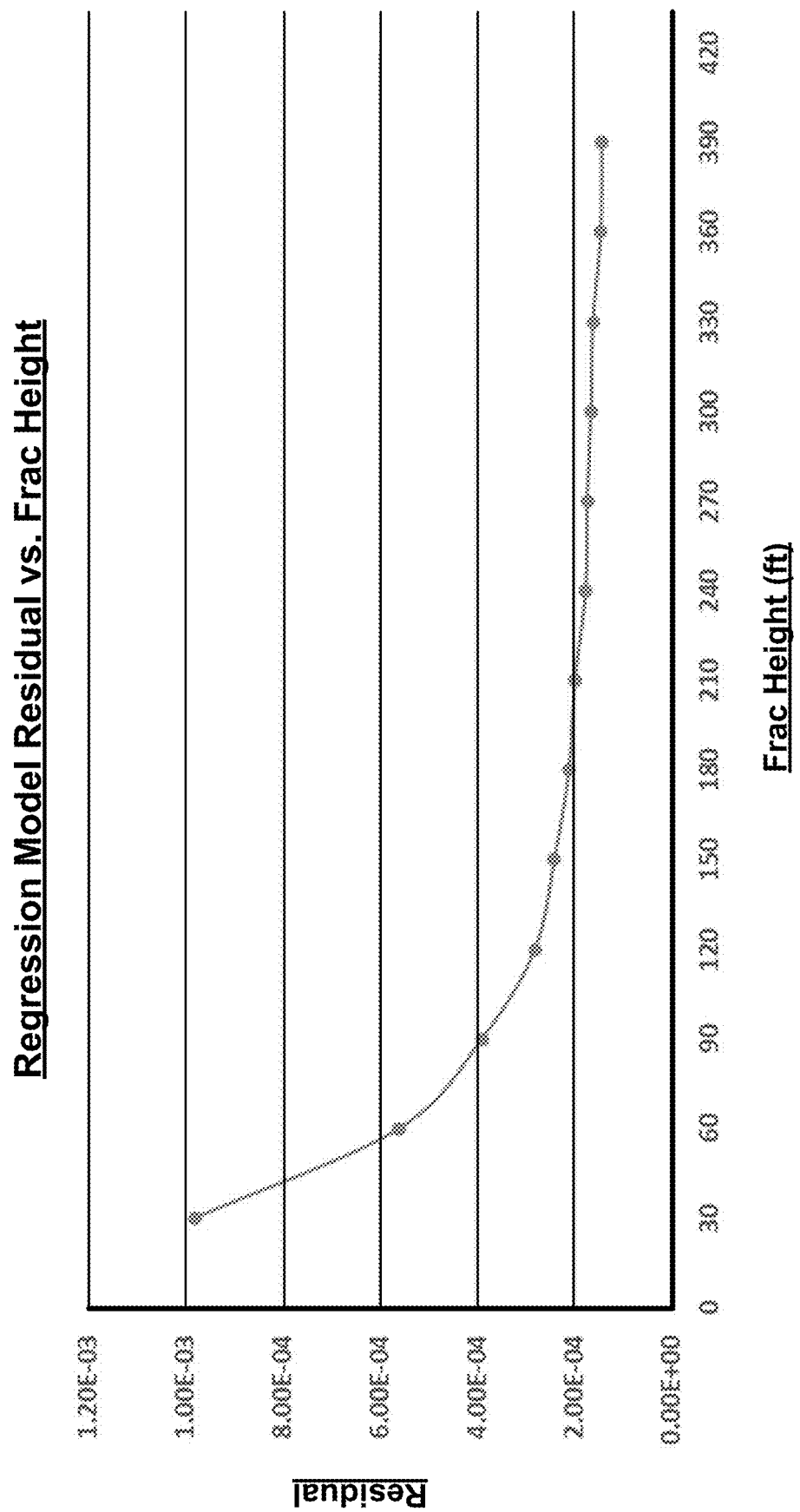
FIG. 14 shows the fracture height evaluation using geochemical fingerprint data.
Figure 15:
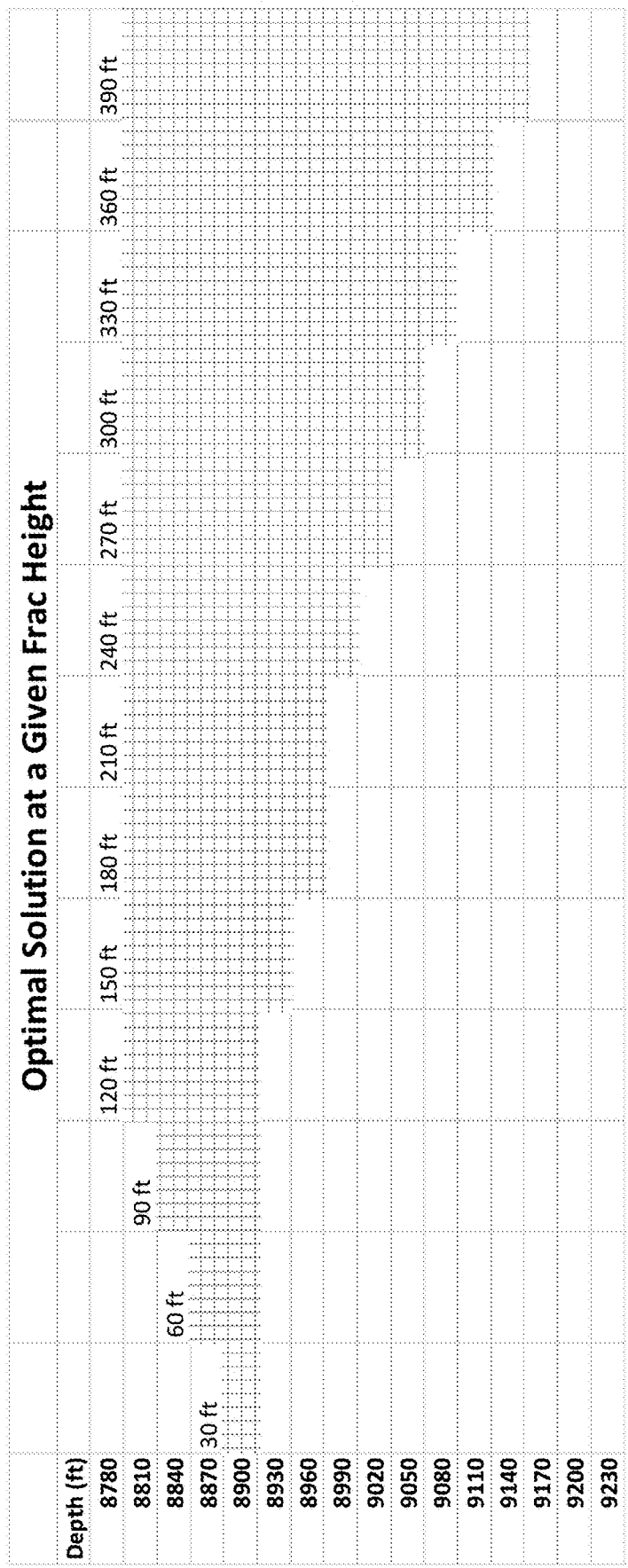
FIG. 15 shows the selection process of cutting end members to be used for the production allocation model of FIG. 13.
Figure 16:
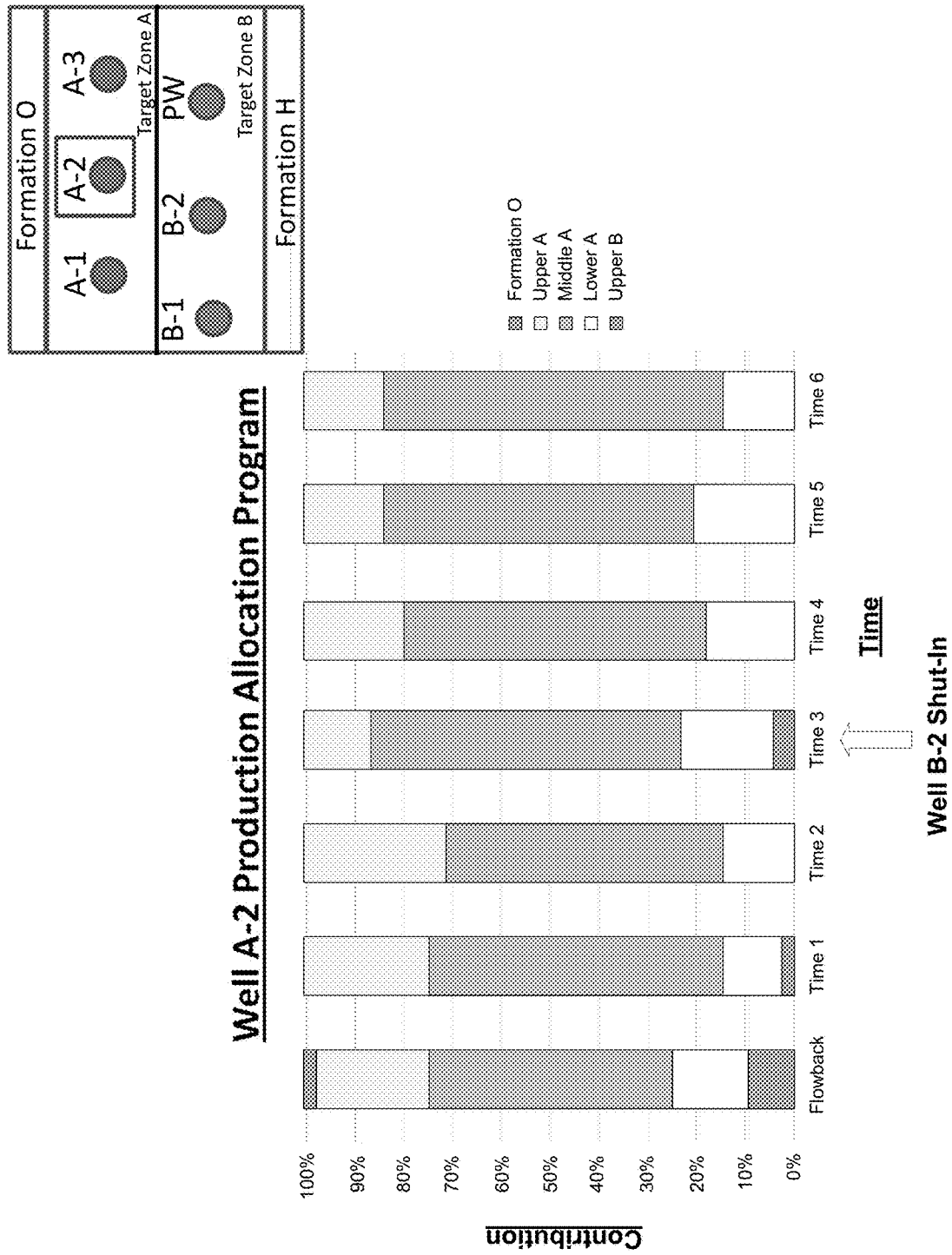
FIG. 16 shows quantitative production allocation results of an example well A-2 using the method and model of FIG. 13.
Figure 17:
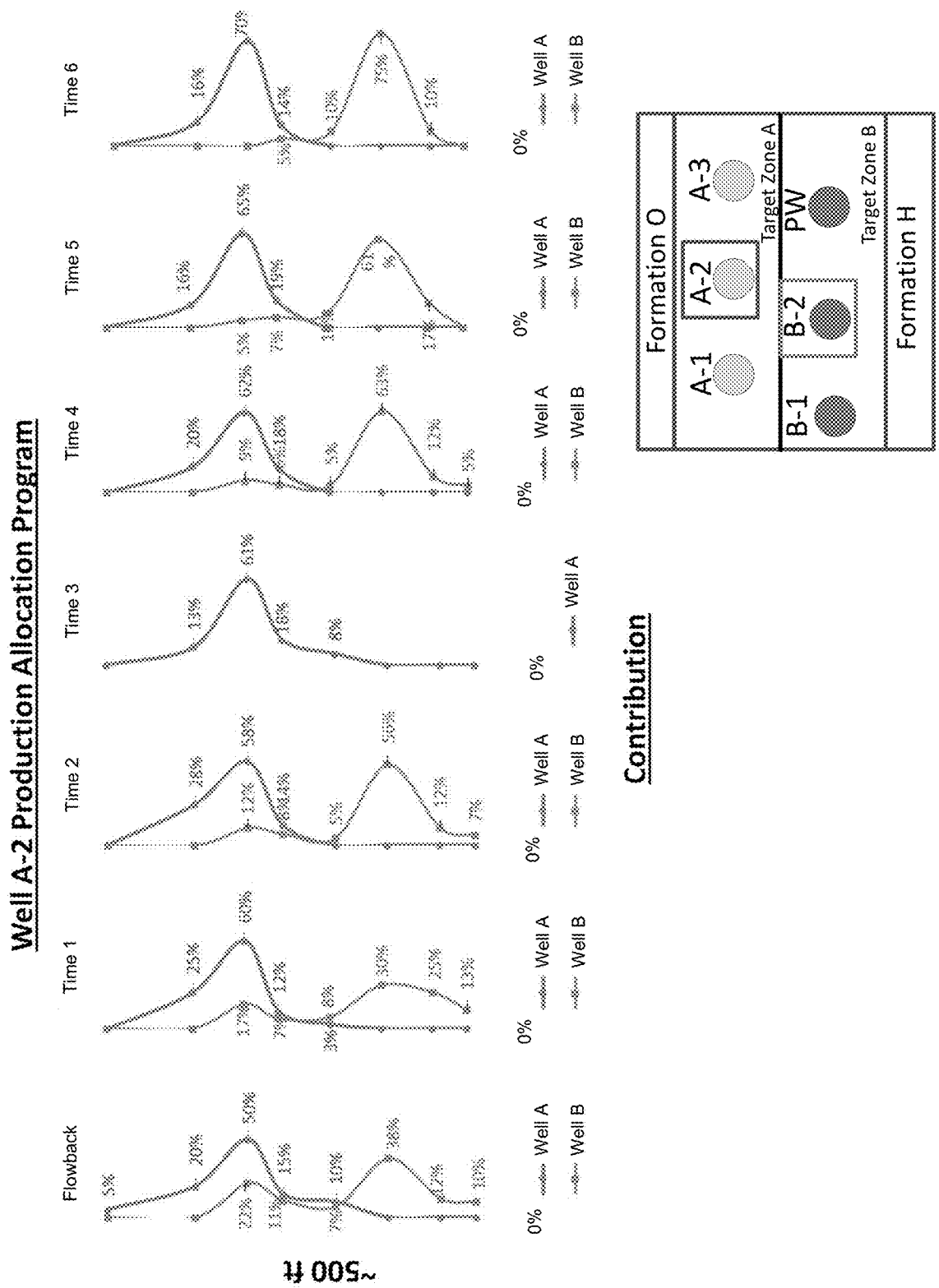
FIG. 17 shows quantitative fracture height evaluation and production allocation results of example wells A-2 and B-2 using the method and model of FIG. 13.

FIG. 14 shows how the residual of the regression model is monitored until an inflection point is reached (in this example, at approximately 120 to 150 feet frac height). In the next step, based on this 120-150 foot range, a selection of end member cutting samples is made (in this example, the samples from 8810 feet to 8930 feet, as seen in FIG. 15) to be used for fine-tuning the regression model. The frac height evaluation and production allocation results from the model were then calculated, as shown in FIGS. 16 and 17.

From those monitoring results, it was concluded that significant production sharing took place between the A-2 and B-2 well. A reservoir management strategy was subsequently developed to improve recovery efficiency of the reservoir.

Example 2—Use of the Method to Evaluate Cluster Efficiency in a Horizontal Well Drilled in An Unconventional Reservoir in Oklahoma The following description provides an example of evaluating cluster along the lateral of a horizontal well drilled in an unconventional reservoir in Oklahoma, USA. Cutting samples approximately 50 grams each (during drilling with water-based mud) were collected along the lateral at approximately 500 foot interval. The cutting samples were rapidly rinsed using tape water, and sealed in isojars to ship to the laboratory. Each cutting sample was sifted to remove any dusts or tiny pieces of contamination, and approximately 30 grams of each sample was cleaned in the laboratory using de-ionized water 5 times, centrifuged using 1000×g for 1 minute, and air-dried under the fume-hood for 18 hours. The cleaned, dried cutting samples were grounded and sifted down to 40-80 mesh size. Approximately 0.1 gram of prepared sample was loaded to the physical extraction instrument (as described in U.S. Provisional Application No. 62/661,109, filed Apr. 23, 2018), and the extractant was measured using GC×GC-FID (Shimadzu GC2030 equipped with Zoex II thermal modulator).

Figure 18:
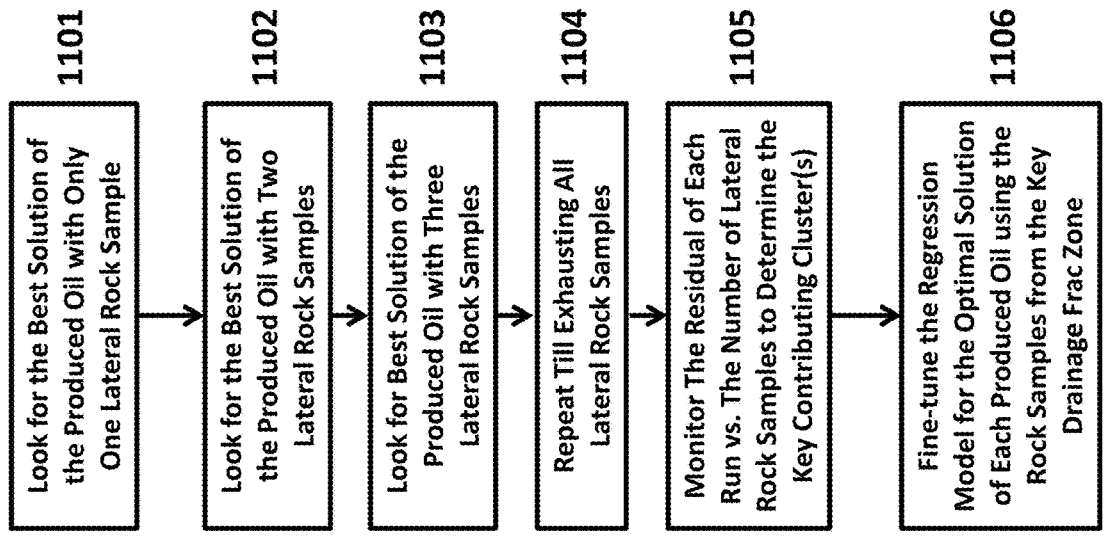
FIG. 18 shows a chart of method steps for a lateral cluster efficiency monitoring model.

Samples from the produced oil from the well was collected for approximately 3 months and shipped to the laboratory where geochemical fingerprint data was collected using GC×GC-FID (Shimadzu GC2030 equipped with Zoex II thermal modulator). The process to evaluate the cluster efficiency and select end member cutting samples to be used for the regression model is illustrated in FIG. 18:

a. Look for the best solution of the produced oil with only one lateral rock sample 1101.

b. Look for the best solution of the produced oil with two lateral rock samples 1102.

c. Look for the best solution of the produced oil with three lateral rock samples 1103.

d. Repeat above steps until exhausting all lateral rock samples 1104.

e. Monitor the residual of each run vs. the number of lateral rock samples to determine the key contributing cluster(s) 1105.

f. Fine time the regression model for the optimal solution of each produced oil sample using the rock samples from the key drainage frac zone 1106.

Figure 19:
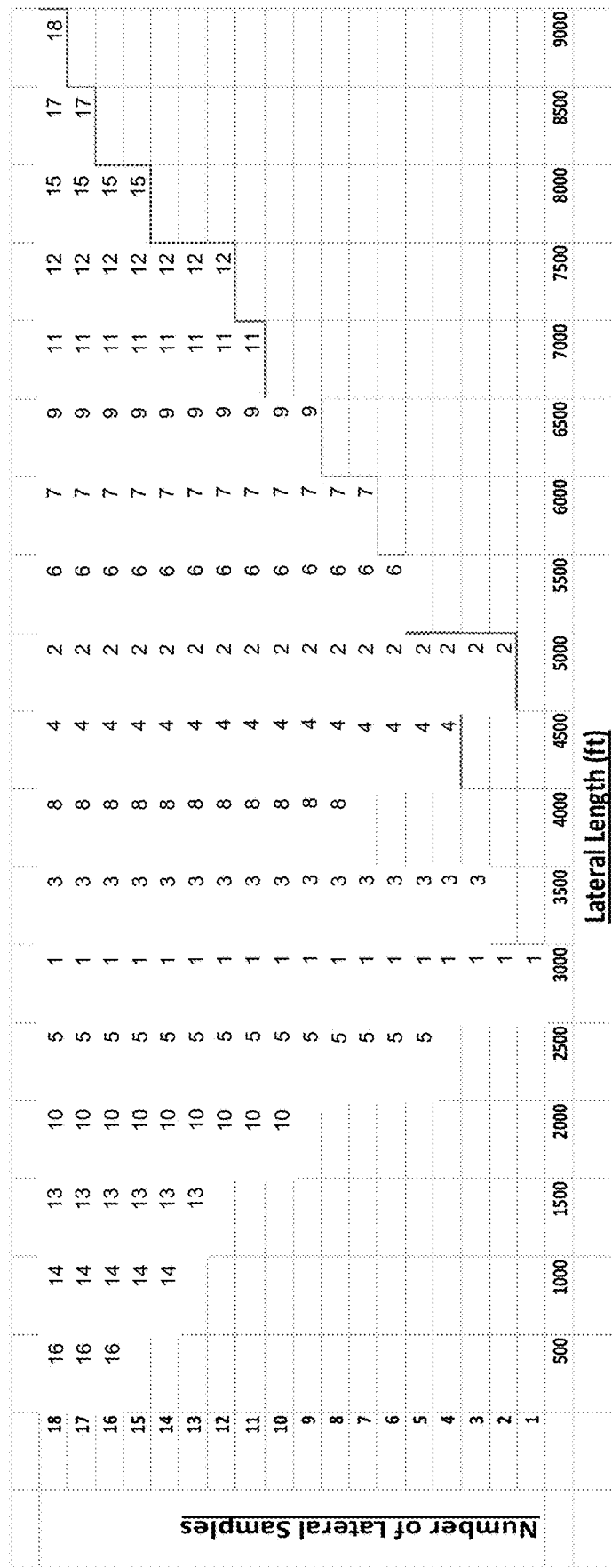
FIG. 19 shows the ranking of the efficiency of each cluster in the lateral well using the method of FIG. 18.

A regression model was built using the lateral cutting samples as pseudo end members to represent each cluster, and the produced oil was back-allocated to the clusters from which they were produced. A ranking of the cluster spacing was then determined as illustrated in FIG. 19.

The key conclusion from this analysis was that the "heel" and the "toe" of the lateral section of the well (i.e., the first 1000 feet closest to the vertical section, and the last 1000 feet) was not very efficient, and thus mostly likely hindered oil production. A strategy was subsequently developed specifically improve the cluster efficiency in the toe and heel sections to increase the oil production.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

One or more of the above-described features and applications may be implemented as software processes that are specified as a set of instructions recorded on a computer readable storage medium (alternatively referred to as computer-readable media, machine-readable media, or machine-readable storage media). When these instructions are executed by one or more processing unit(s) (e.g., one or more processors, cores of processors, or other processing units), they cause the processing unit(s) to perform the actions indicated in the instructions.

In one or more implementations, a computer program product (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

In order to provide a context for the various computer-implemented aspects of the invention, the following discussion provides a brief, general description of a suitable computing environment in which the various aspects of the present invention may be implemented. A computing system environment is one example of a suitable computing environment, but is not intended to suggest any limitation as to the scope of use or functionality of the invention. A computing environment may contain any one or combination of components discussed below, and may contain additional components, or some of the illustrated components may be absent. Various embodiments of the invention are operational with numerous general purpose or special purpose computing systems, environments or configurations. Examples of computing systems, environments, or configurations that may be suitable for use with various embodiments of the invention include, but are not limited to, personal computers, laptop computers, computer servers, computer notebooks, hand-held devices, microprocessor-based systems, multiprocessor systems, TV set-top boxes and devices, programmable consumer electronics, cell phones, personal digital assistants (PDAs), tablets, smart phones, touch screen devices, smart TV, internet enabled appliances, internet enabled security systems, internet enabled gaming systems, internet enabled watches; internet enabled cars (or transportation), network PCs, minicomputers, mainframe computers, embedded systems, virtual systems, distributed computing environments, streaming environments, volatile environments, and the like.

Embodiments of the invention may be implemented in the form of computer-executable instructions, such as program code or program modules, being executed by a computer, virtual computer, or computing device. Program code or modules may include programs, objects, components, data elements and structures, routines, subroutines, functions and the like. These are used to perform or implement particular tasks or functions. Embodiments of the invention also may be implemented in distributed computing environments. In such environments, tasks are performed by remote processing devices linked via a communications network or other data transmission medium, and data and program code or modules may be located in both local and remote computer storage media including memory storage devices such as, but not limited to, hard drives, solid state drives (SSD), flash drives, USB drives, optical drives, and internet-based storage (e.g., "cloud" storage).

In one embodiment, a computer system comprises multiple client devices in communication with one or more server devices through or over a network, although in some cases no server device is used. In various embodiments, the network may comprise the Internet, an intranet, Wide Area Network (WAN), or Local Area Network (LAN). It should be noted that many of the methods of the present invention are operable within a single computing device.

A client device may be any type of processor-based platform that is connected to a network and that interacts with one or more application programs. The client devices each comprise a computer-readable medium in the form of volatile and/or nonvolatile memory such as read only memory (ROM) and random access memory (RAM) in communication with a processor. The processor executes computer-executable program instructions stored in memory. Examples of such processors include, but are not limited to, microprocessors, ASICs, and the like.

Client devices may further comprise computer-readable media in communication with the processor, said media storing program code, modules and instructions that, when executed by the processor, cause the processor to execute the program and perform the steps described herein. Computer readable media can be any available media that can be accessed by computer or computing device and includes both volatile and nonvolatile media, and removable and non-removable media. Computer-readable media may further comprise computer storage media and communication media. Computer storage media comprises media for storage of information, such as computer readable instructions, data, data structures, or program code or modules. Examples of computer-readable media include, but are not limited to, any electronic, optical, magnetic, or other storage or transmission device, a floppy disk, hard disk drive, CD-ROM, DVD, magnetic disk, memory chip, ROM, RAM, EEPROM, flash memory or other memory technology, an ASIC, a configured processor, CDROM, DVD or other optical disk storage, magnetic cassettes, magnetic tape, magnetic disk storage or other magnetic storage devices, or any other medium from which a computer processor can read instructions or that can store desired information. Communication media comprises media that may transmit or carry instructions to a computer, including, but not limited to, a router, private or public network, wired network, direct wired connection, wireless network, other wireless media (such as acoustic, RF, infra-red, or the like) or other transmission device or channel. This may include computer readable instructions, data structures, program modules or other data in a modulated data signal such as a carrier wave or other transport mechanism. Said transmission may be wired, wireless, or both. Combinations of any of the above should also be included within the scope of computer readable media. The instructions may comprise code from any computer-programming language, including, for example, C, C++, C #, Visual Basic, Java, and the like.

Components of a general purpose client or computing device may further include a system bus that connects various system components, including the memory and processor. A system bus may be any of several types of bus structures, including, but not limited to, a memory bus or memory controller, a peripheral bus, and a local bus using any of a variety of bus architectures. Such architectures include, but are not limited to, Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computing and client devices also may include a basic input/output system (BIOS), which contains the basic routines that help to transfer information between elements within a computer, such as during start-up. BIOS typically is stored in ROM. In contrast, RAM typically contains data or program code or modules that are accessible to or presently being operated on by processor, such as, but not limited to, the operating system, application program, and data.

Client devices also may comprise a variety of other internal or external components, such as a monitor or display, a keyboard, a mouse, a trackball, a pointing device, touch pad, microphone, joystick, satellite dish, scanner, a disk drive, a CD-ROM or DVD drive, or other input or output devices. These and other devices are typically connected to the processor through a user input interface coupled to the system bus, but may be connected by other interface and bus structures, such as a parallel port, serial port, game port or a universal serial bus (USB). A monitor or other type of display device is typically connected to the system bus via a video interface. In addition to the monitor, client devices may also include other peripheral output devices such as speakers and printer, which may be connected through an output peripheral interface.

Client devices may operate on any operating system capable of supporting an application of the type disclosed herein. Client devices also may support a browser or browser-enabled application. Examples of client devices include, but are not limited to, personal computers, laptop computers, personal digital assistants, computer notebooks, hand-held devices, cellular phones, mobile phones, smart phones, pagers, digital tablets, Internet appliances, and other processor-based devices. Users may communicate with each other, and with other systems, networks, and devices, over the network through the respective client devices.

Thus, it should be understood that the embodiments and examples described herein have been chosen and described in order to best illustrate the principles of the invention and its practical applications to thereby enable one of ordinary skill in the art to best utilize the invention in various embodiments and with various modifications as are suited for particular uses contemplated. Even though specific embodiments of this invention have been described, they are not to be taken as exhaustive. There are several variations that will be apparent to those skilled in the art.

What is claimed is:

1. A method of three-dimensional reservoir monitoring in a reservoir, comprising the steps of:
   obtaining a plurality of rock samples from a part of a well extending through a plurality of formations;
   obtaining a plurality of oil samples from the well;
   extracting hydrocarbons from the rock samples;
   obtaining high-resolution geochemical fingerprint data from the extracted hydrocarbons from said plurality of rock samples using two-dimensional gas chromatography;
   obtaining high-resolution geochemical fingerprint data from said plurality of oil samples using two-dimensional gas chromatography;
   pre-processing the high-resolution geochemical fingerprint data from the extracted hydrocarbons from said plurality of rock samples, and the high-resolution geochemical fingerprint data from said plurality of oil samples, wherein said pre-processing of the high-resolution geochemical fingerprint data from said plurality of oil samples includes peak screening; and
   allocating oil from the well to particular formations or sections of formations from said plurality of formations based upon the high-resolution geochemical fingerprints of the extracted hydrocarbon profiles and the oil sample profiles.

2. The method of claim 1, further comprising the steps of:
   obtaining a plurality of rock samples from adjacent wells drilled in said plurality of formations;
   extracting hydrocarbons from the plurality of rock samples from said adjacent wells;
   profiling the extracted hydrocarbons from said the plurality of rock samples from said adjacent wells;
   obtaining a plurality of oil samples from said adjacent wells; and
   profiling said plurality of oil samples from said adjacent wells.

3. The method of claim 1, wherein said high-resolution geochemical fingerprinting comprises GC×GC.

4. The method of claim 1, further comprising the step of preprocessing the geochemical fingerprinting data.

* * * * *